United States Patent
Paul et al.

(10) Patent No.: US 9,513,204 B2
(45) Date of Patent: Dec. 6, 2016

(54) DEVICE AND METHOD FOR MONITORING ROOMS EQUIPPED WITH HIGH-VOLTAGE APPARATUSES

(71) Applicants: Thomas Alfred Paul, Waedenswil (CH); Axel Kramer, Wettingen (CH); Mathias Ingold, Unterengstringen (CH)

(72) Inventors: Thomas Alfred Paul, Waedenswil (CH); Axel Kramer, Wettingen (CH); Mathias Ingold, Unterengstringen (CH)

(73) Assignee: ABB Technology AG (CH)

( * ) Notice: Subject to any disclaimer, the term of this patent is extended or adjusted under 35 U.S.C. 154(b) by 36 days.

(21) Appl. No.: 14/638,712

(22) Filed: Mar. 4, 2015

(65) Prior Publication Data

US 2015/0247788 A1 Sep. 3, 2015

Related U.S. Application Data

(63) Continuation of application No. PCT/EP2013/068281, filed on Sep. 4, 2013, and a continuation of application No. PCT/EP2013/062683, filed on Jun. 19, 2013, and a continuation of application No. PCT/EP2012/067219, filed on Sep. 4, 2012.

(30) Foreign Application Priority Data

Jun. 19, 2013 (EP) ..................................... 13172591

(51) Int. Cl.
*G01N 21/00* (2006.01)
*G01N 15/06* (2006.01)
(Continued)

(52) U.S. Cl.
CPC ................ *G01N 15/06* (2013.01); *E04H 5/02* (2013.01); *G01N 21/31* (2013.01); *G01N 21/33* (2013.01);
(Continued)

(58) Field of Classification Search
CPC .. G01N 21/3504; G01N 21/31; G01N 15/06; E04H 5/02; E04H 5/06; H01H 33/04; G01M 3/20
See application file for complete search history.

(56) References Cited

U.S. PATENT DOCUMENTS 4,052,555 A  10/1977 Mears et al.
4,445,364 A * 5/1984 Stieff ...................... G01M 3/20
                                                    222/54

(Continued)

FOREIGN PATENT DOCUMENTS

DE              4412012 A1    10/1995
DE        202009009305 U1    11/2009
(Continued)

OTHER PUBLICATIONS

Kurte, et al., "Application of Infrared Spectroscopy to Monitoring Gas Insulated High-Voltage Equipment: Electrode Material-Dependent SF6 Decomposition", Anal Bioanal Chem (2002) pp. 639-646.
(Continued)

*Primary Examiner* — Tarifur Chowdhury
*Assistant Examiner* — Maurice Smith
(74) *Attorney, Agent, or Firm* — St. Onge Steward Johnston & Reens LLC

(57) ABSTRACT

A monitoring device for determining the concentration of a dielectric insulation fluid such as a perfluoroketones in a room housing at least one high-voltage electrical apparatus and being accessible by humans essentially without modifying the room conditions, for example the room being a part of an air-insulated substation, with the monitoring system including one or more sensors for determining an emission and/or absorption of the dielectric insulation fluid molecules at at least one wavelength or wavelength band of the electromagnetic wave spectrum.

29 Claims, 11 Drawing Sheets

(51) Int. Cl.
  *G01N 21/3504* (2014.01)
  *G01N 21/31* (2006.01)
  *G01N 21/33* (2006.01)
  *G01N 21/3581* (2014.01)
  *E04H 5/02* (2006.01)
  *H01H 33/56* (2006.01)

(52) U.S. Cl.
  CPC ...... *G01N 21/3504* (2013.01); *G01N 21/3581* (2013.01); *G01N 2015/0693* (2013.01); *H01H 33/563* (2013.01)

(56) References Cited

U.S. PATENT DOCUMENTS

| | | | |
|---|---|---|---|
| 5,218,212 A | 6/1993 | Sato et al. | |
| 6,773,558 B2* | 8/2004 | Agnew | H01J 37/32422 204/192.35 |
| 2002/0095262 A1 | 7/2002 | Chetay et al. | |
| 2008/0135817 A1 | 6/2008 | Luly et al. | |
| 2008/0295580 A1 | 12/2008 | Minor et al. | |

FOREIGN PATENT DOCUMENTS

| | | |
|---|---|---|
| FR | 2955970 A1 | 8/2011 |
| GB | 2126790 A | 3/1984 |
| JP | S57100338 A | 6/1982 |
| WO | 2007121593 A1 | 11/2007 |
| WO | 2013087700 A1 | 6/2013 |

OTHER PUBLICATIONS

International Preliminary Report on Patentability Application No. PCT/EP2013/068281 Completed: Dec. 17, 2014 37 pages.
International Search Report and Written Opinion of the International Searching Authority Application No. PCT/EP2012/067219 Completed: May 14, 2013; Mailing Date: May 23, 2013 14 pages.

* cited by examiner

DEVICE AND METHOD FOR MONITORING ROOMS EQUIPPED WITH HIGH-VOLTAGE APPARATUSES

FIELD OF THE INVENTION

The present invention relates to a device and a method for monitoring rooms that are equipped with at least one medium-voltage and/or high-voltage device or apparatus and that are accessible by humans essentially without modifying the room atmospheric conditions. Examples of such rooms are air-insulated converter stations or other rooms housing high-voltage apparatuses and in particular switching devices.

BACKGROUND OF THE INVENTION

Organic fluorine compounds and specifically perfluoroketones (PFKs) are suitable insulation gases for electrical apparatus, such as medium-voltage or high-voltage switchgears. The ketones can be described by the number of carbon atoms in their main chain, for example as C5, C6, or C7 indicating that 5 or 6 or 7 carbon atoms are present in their main chain. Gas mixtures containing PFKs are preferred over pure $SF_6$ and over $SF_6$ mixtures due to their much lower global warming potential.

PFK mixtures are also relevant as replacement gases for air-insulated converter stations having the benefit of increased dielectric strength without the need to increase operating pressure and without much adverse environmental impact. This is of particular relevance for air-insulated converter stations. As such stations need to be accessible by humans and as they are not leakage-free, they cannot be filled with $SF_6$. Consequently distances between live parts must be chosen to be compatible with air insulation leading to a comparatively large footprint of the station. The use of PFK/carrier gas mixtures has the potential of reducing the footprint of large air-insulated stations substantially. Another advantage of the use of PFK/carrier-gas mixtures is their non-toxicity and reduced or negligible environmental impact.

Contrary to the use in for example hermetically sealed switches and the like, when used for rooms or other enclosures of large volume any PFK/carrier gas mixtures will require more often filling or replenishing. Basis for such operations is an accurate measurement of the PFK content in the room atmosphere, in particular room air, on an essentially continuous basis.

Up to now perfluoroketones have mainly been used as refrigerants, heat transfer fluids or fire extinguishing media. There are devices available on the market that address sensing of this class of substances. For example, the company Bacharach offers a room monitor (HG-halogen gas monitor/leak monitor for refrigerant gases including the PFK C6 named Novec™ 649) which is based on an MIR (mid-infrared) absorption measurement. Further portable FTIRs (Fourier-transform infrared) spectrometers are available commercially for refrigerant leak detection, e.g. the MIRAN from the company Thermo Scientific™.

Room monitoring systems using several infrared sensors for refrigerant leaks are known for example from the brochure "Mechanical Equipment Rooms" by Honeywell™, 2011. The system described includes a plurality of different sensors connected to a controller. The controller has a relay side used to activate or deactivate alarms, vents, machinery etc.

The invention starts from JP S57 100388 which discloses an infrared laser beam for monitoring combustible or explosive gas in a semiclosed space, such as an underground market, and to shut down leakage of the gas and eventually to ventilate it out of the semiclosed space.

US 2003/0235026 discloses a converter station housed in a closed multistory building. The converter station is equipped with electrical apparatuses that are encapsulated and SF6-gas-insulated or are air-insulated.

SUMMARY OF THE INVENTION

In view of the above it is an objective of the present invention to provide an improved device and method for monitoring accurately the concentration of a dielectric insulation fluid in rooms housing at least one medium-voltage or high-voltage electrical apparatus, wherein the rooms are accessible by humans, preferably without modifying the room atmospheric conditions.

This objective is achieved by the subject-matter of the independent claims. Embodiments arise from dependent claims, their combinations, and from the description and the figures.

Throughout this application medium-voltage or high-voltage is to be understood to comprise voltages of 10 kV or more. Thus, the term high-voltage may also comprise medium-voltage applications known in electrical engineering.

According to a first aspect of the invention, there is provided a monitoring device for determining or monitoring a concentration of a dielectric insulation medium, in particular dielectric insulation fluid or gas, in a room housing at least one medium-voltage or high-voltage electrical apparatus, wherein the room is accessible by humans, and the monitoring system includes one or more sensors for determining in a non-local manner an averaged concentration-dependent electromagnetic property of the molecules present in the dielectric insulation medium at at least one wavelength or wavelength band of the electromagnetic wave spectrum.

In embodiments, the monitoring device includes components that are fixedly mounted in the room; and/or the monitoring device includes components that are temporarily mounted inside the room; and/or the monitoring device is installed inside the room.

In embodiments, the monitoring device is adapted to the room to monitor an average, in particular a spatially continuous average and/or a sampling-point average, of the concentration of the molecules (PFK), which are present in the dielectric insulation medium in the room, along an averaging path length in the room. In particular, the averaging path length is of the order of a dimension of the room, or of a dimension of a door for accessing the room by a human, or of a dimension of the at least one medium-voltage or high-voltage electrical apparatus.

In embodiments, the monitoring device is adapted:
  to determine as the concentration-dependent electromagnetic property an emission and/or an absorption and/or a transmission and/or a scattering by the molecules to be monitored; and/or
  to determine the concentration of such molecules, that are part of a dielectric insulation component C1 other than air and/or that provide to the dielectric insulation medium a dielectric strength greater than the dielectric strength of air; and/or
  to determine the concentration of such molecules, that are not part of a background gas present in the dielectric insulation medium, in particular that are not any one of the group consisting of: nitrogen, oxygen carbon dioxide; and/or to determine the concentration of such molecules that originate from chemical transformation of the dielectric insulation medium under arcing or ageing or chemical reactions in the room; and/or to determine the concentration of the molecules of an organic fluorine compound, in particular of a partly fluorinated or fully fluorinated compound of an olefine, an alkane, a ketone or polyketone, an ether or polyether, and any mixtures thereof; and/or to determine the concentration of fluoroketone molecules, in particular of a partly fluorinated or fully fluorinated fluoroketone comprising exactly 5 or exactly 6 or exactly 7 or exactly 8 carbon atoms and any mixtures thereof.

In embodiments, the monitoring device is adapted to determine the concentration of at least one component selected from the group consisting of:

partially or fully fluorinated ethers; in particular: hydrofluoroethers, hydrofluoro monoethers, hydrofluoro monoethers containing at least 3 carbon atoms, perfluoro monoethers, perfluoro monoethers containing at least 4 carbon atoms, fluorooxiranes, perfluorooxiranes, hydrofluorooxiranes, perfluorooxiranes comprising from three to fifteen carbon atoms, hydrofluorooxiranes comprising from three to fifteen carbon atoms, and mixtures thereof;

partially or fully fluorinated ketones; in particular: hydrofluoro monoketones, perfluoro monoketones, perfluoro monoketones comprising at least 5 carbon atoms, and mixtures thereof;

fluoroolefins; in particular: perfluoroolefines, hydrofluoroolefins (HFO), hydrofluoroolefins (HFO) comprising at least three carbon atoms, hydrofluoroolefins (HFO) comprising exactly three carbon atoms, trans-1,3,3,3-tetrafluoro-1-propene (HFO-1234ze), 2,3,3,3-tetrafluoro-1-propene (HFO-1234yf), and mixtures thereof; and mixtures thereof.

In embodiments, the sensor has sensing means for measuring an averaged emission and/or an averaged absorption and/or an averaged transmission by the molecules along a substantial length of the room, in particular along a length larger than a size of a door for accessing the room by a human, more particularly along a length larger than a quarter length or even a half length of the room.

In embodiments, the sensor has sensing means that
are permanently installed in the room; and/or
are arranged in an eye-safe region of the room; and/or
are arranged in a region of the room that is not accessible by up-right walking humans; and/or
are arranged in regions of high or above-average field strengths in the room; and/or that
are arranged in proximity of, in particular along, non-encapsulated components of the electrical apparatus.

In embodiments, the system includes components that are fixedly mounted in the room. Hence these components are mounted onto a ceiling, a wall, a floor or other part of the permanent room installations, in particular such that a collimated beam of electromagnetic radiation can be transmitted across a free-space part or a full length of the room.

In embodiments, the system monitors the concentration continuously or at least at intervals of less than 10 minutes. It is particularly preferred if, in addition or alternatively to the continuous monitoring, the system is configured to initiate a measurement triggered by a change in the perimeter integrity of the room. Such a change can for example include the opening and/or closing of a door as detected by a door switch etc.

In embodiments, the dielectric insulation fluid can be an organic fluorine compound, for example a partly fluorinated or fully fluorinated (=perfluorinated) compound of an olefine, an alkane, a ketone or polyketone, an ether or polyether, and any mixtures thereof. Most preferred embodiments are perfluoroketones having from 5 carbon atoms to 9 carbon atoms that shall be monitored. Examples of the perfluoroketones having from 5 carbon atoms to 9 carbon atoms include $CF_3CF_2C(O)CF(CF_3)_2$, $(CF_3)_2CFC(O)CF(CF_3)_2$, $CF_3(CF_2)_2C(O)CF(CF_3)_2$, $CF_3(CF_2)_3C(O)CF(CF_3)_2$, $CF_3(CF_2)_5C(O)$ $CF_3$, $CF_3CF_2C(O)$ $CF_2CF_2CF_3$, $CF_3C(O)CF(CF_3)_2$, and perfluorocyclohexanone and others as referred to in this specification. These compounds may be used alone or in combination with one another, and/or in mixtures with a carrier or background gas.

In an embodiment of this aspect of the invention, the at least one wavelength or wavelength band is in the range of 200 nm to 20000 nm, for example in the range of 200 nm to 400 nm and/or 1850 nm to 1950 nm and/or 5000 nm to 20000 nm.

In embodiments, the sensor includes a radiation source and/or a spectral filter that is or are tuned each or both in combination to at least one wavelength or wavelength band in the spectral range of 200 nm to 20,000 nm, for example in at least one of the spectral ranges of 200 nm to 400 nm, 1850 nm to 1950 nm, and 5000 nm to 20000 nm.

In embodiments, the one or more sensors is or are designed to perform in the room to be monitored the non-local measurement that may comprise a plurality of single-location measurements and/or a measurement averaged across a substantial room section, for example averaged across essentially at least a quarter or, even preferably across at least a half length of the full room extent. For example, the measurement locations include particularly relevant locations along busbars or outer walls or along a perimeter of the room. Measurements along busbars or generally along electrical active parts or along non-encapsulated components of electrical active parts are relevant, because this allow to control the molecule concentration and hence dielectric strength of the dielectric insulation medium in regions of increased dielectric stress; and the electromagnetic radiation or optical beam does not adversely affect the dielectric strength of the dielectric insulation medium to be monitored. Measurements in non-accessible or difficult-to-access regions are relevant, because this provides safety to personnel entering the room against the electromagnetic radiation or free-space laser beams used for the non-local averaging measurement of the molecular concentrations.

In embodiments, the sensor includes a collimated electromagnetic beam sampling the room at more than one location or continuously across at least part of the room. The collimated beam can be confined within an optical fiber arranged across at least a part or region of the room. Thus, the beam is favourably protected against accidental human interference or manipulation.

In an embodiment, the sensor includes a device to measure or estimate the total intensity or power of an emitted or absorbed or transmitted electromagnetic radiation.

To save power the sensor can be operated such that radiation is emitted or measured in a pulsed manner.

In an embodiment, the monitor system includes a distributed temperature sensing system. Such a system can be used to detect whether the room temperature is close or below the condensation point of the gas mixture in the room.

In another embodiment of this aspect of the invention, the monitoring system is part of or is connected to a safety control system initiating a mitigating response to changes in the concentrations of the dielectric insulation fluid, including for example the release of additional dielectric insulation fluid into the room or the redistribution of atmosphere, in particular air, within the room. For example, the additional dielectric insulation fluid may be sourced from a storage container having fresh and/or recollected dielectric insulation fluid, in particular in liquid form.

A second aspect of the invention relates to a building, in particular converter building, comprising at least one room having a solid room wall enclosing an interior space and at least one electrical active part contained in the interior space, the room wall having at least one opening, which is designed such that it allows a human to enter the interior space, wherein the opening is sealable, the room wall encloses the interior space in a gas-tight manner when the opening is sealed, and the interior space contains a dielectric insulation medium comprising a dielectric insulation component C1 other than air, wherein further the room is equipped with a monitoring device, in particular according to any one of the preceding claims, for monitoring a concentration of molecules present in the dielectric insulation medium, and the monitoring device comprises at least one sensor for determining a concentration-dependent electromagnetic property of the molecules (PFK) present in the dielectric insulation medium at at least one wavelength or wavelength band of the electromagnetic wave spectrum.

Embodiments of the building are given in the dependent claims and particularly comprise any monitoring device as disclosed in this application.

In embodiments of the building, the room contained in the building to be monitored comprises a non-toxic, breathable atmosphere, particularly at a pressure close to ambient atmospheric pressure; and/or the room is accessible by humans essentially without modifying room atmospheric conditions; and/or the room is accessible by humans without deteriorating a dielectric strength of the room atmosphere below an operational threshold value; and/or the room is accessible by humans while maintaining a dielectric strength of the room atmosphere above a dielectric strength of air.

In embodiments of the building, the monitoring device arranged in the room in the building has sensing means for measuring a light power that is a concentration-dependent function of the optical emission and/or optical absorption and/or optical transmission by the molecules to be monitored.

In embodiments of the building, the molecules to-be-monitored are part of the dielectric insulation component C1 other than air; and/or the molecules are not part of a background gas present in the dielectric insulation medium and in particular wherein the molecules are not any of the group consisting of: nitrogen, oxygen carbon dioxide.

In embodiments of the building, the molecules to be monitored provide a dielectric strength to the dielectric insulation medium larger than the dielectric strength of air.

In embodiments of the building, the monitoring device is arranged inside the room in regions of high or above-average dielectric field strengths and/or is arranged in proximity of, in particular along, non-encapsulated components of the electrical apparatus.

In embodiments of the building, the monitoring device is permanently installed inside the room.

A third aspect of the invention relates to a method of monitoring the concentration of molecules present in a dielectric insulation fluid in a room, in particular the method for being executed by a monitoring device as disclosed in this application, the room housing at least one medium-voltage or high-voltage electrical apparatus and being accessible by humans, the method comprising the steps of monitoring in-situ the concentration of the molecules in the dielectric insulation medium, in particular dielectric insulation fluid or gas, by determining in a non-local manner an averaged concentration-dependent electromagnetic property of the molecules in the dielectric insulation medium at at least one wavelength of the electromagnetic wave spectrum.

In embodiments of the method, the determining the concentration-dependent electromagnetic property comprises determining an emission and/or an absorption and/or a transmission and/or a scattering by the molecules.

In embodiments of the method, the determining comprises measuring an emission and/or an absorption and/or a transmission by the molecules along a substantial length of the room, in particular along a length larger than a size of a door for accessing the room by a human, more particularly along a length larger than a quarter length or even a half length of the room.

In embodiments, the method further comprises the step of delivering the dielectric insulation medium to the room by controlling a supply of the dielectric insulation medium.

In embodiments, the method further comprises the step of monitoring a temperature of the room at more than one location to determine whether the temperature at a location is close or below the condensation temperature of a standard atmosphere comprising a desired concentration of the dielectric insulation fluid.

In embodiments, the molecules in the dielectric insulation medium are an organic fluorine compound, particularly a perfluoroketone, more particularly a partly fluorinated or fully fluorinated fluoroketone comprising exactly 5 or exactly 6 or exactly 7 or exactly 8 carbon atoms and any mixtures thereof.

In embodiments of the monitoring device, building and method, the monitoring device or building with monitoring device or method of monitoring is for monitoring and/or controlling in-situ a (e.g. average) dielectric strength of the dielectric insulation medium. This allows to maintain the dielectric strength inside the room above a threshold required for operating the electrical active parts.

In other embodiments, at least a part of the optical sensor, in particular a measurement and/or reference channel or beam of the optical sensor, is separated from the room housing the electrical apparatus by an insulation-fluid-permeable protective cover, in particular an insulation-fluid-permeable and particle-impermeable protective cover. This protective cover is adapted to protect the optical sensor from particle contamination present in the room. It separates the monitoring device, in particular an optical beam and/or optical components of the sensor, from the surrounding part of the room. In addition, protective means such as gas adsorbers (e.g. comprising a zeolite) can be provided, if contaminants, e.g. decomposition gases, are created inside the room which may damage the optical sensor. Thus, an insulation-fluid-permeable and yet particle-impermeable protective cover is realized.

In other embodiments, a or the optical measurement comprises an optical measurement channel at a first wavelength (e.g. that is absorbed by the first fluid component (A)), and an optical reference channel at a second wavelength that is not modified, in particular absorbed, by the first fluid component (A).

Furthermore, it can be important to keep humidity levels in the room rather low. For example, condensation of water increases the risk of flashovers. As well, perfluorketones as insulation fluid components could be deteriorated or be decomposed in the presence of water, thereby forming various undesirable contaminants. As a consequence, the dielectric performance of the insulation gas may be reduced.

Therefore, in embodiments, a or the control system of the monitoring device is connected to at least one humidity sensor in the room; in particular the humidity sensor, as further detailed in connection with the figures, being selected from the group consisting of:

A capacitive humidity sensor,
A resistive humidity sensor,
An oscillating resonator coated with a hygroscopic layer,
A thermal conductivity sensor,
A or the optical sensor,
and combinations thereof.

The above and other aspects of the present invention together with further embodiments, examples and applications of the present invention are described in further details and purely exemplarily in the following description and figures.

DETAILED DESCRIPTION OF THE INVENTION

Figure 4:
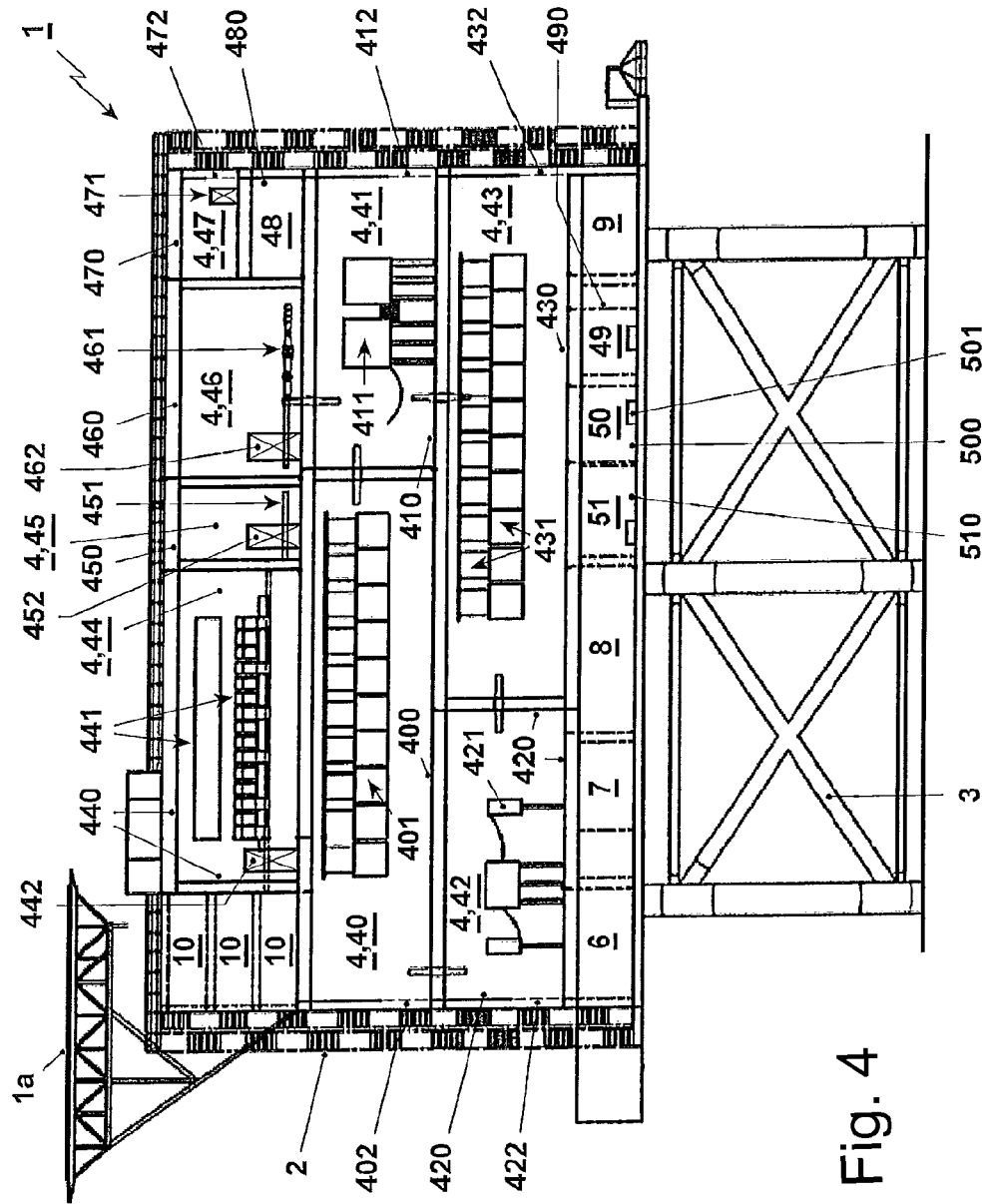
FIG. 4 shows a converter building (e.g. HVDC offshore station) according to the present invention in cross-sectional view.

An air-insulated converter station, e.g. as shown in FIG. 4, is a one- or multi-storied building 1 with building walls 2, here on a basement construction 3 and equipped with a helicopter platform 1a. The converter building 1 or general building 1 can have a number of different rooms 4; 40, 41, 42, 43, 44, 45, 46, 47 housing at least one medium-voltage or high-voltage electrical apparatus 401, 411, 421, 431; 441, 451, 461, 471. The rooms 4; 40-47 may in this case for example be a valve hall 40, 43, a reactor hall 41, a DC hall 42, a GIS hall 44, a cable hall 45, a transformer hall 46, and a transformer hall 47. Such rooms 4; 40-47 can accordingly be equipped with for example any of or a combination of power semiconductor converter valves 401, 431, a reactor 411, DC electrical active parts 421, a GIS switchgear 441, high-voltage cables 451, switches or circuit breakers, busbars, transformers 461, capacitors, arrestors 471, and/or resistors. The electrical active parts 401, 411, 421, 431; 441, 451, 461, 471 may comprise encapsulated components 401A and non-encapsulated components 401B (see e.g. FIG. 1A). Such rooms 4; 40-47 are separated by room walls 400, 410, 420, 430; 440, 450, 460, 470 and can be accessible by humans, for example personnel, via openings or doors 402, 412, 422, 432; 442, 452, 462, 472 that in particular can be equipped with door sealing means 403, 413, 423, 433; 443, 453, 463, 473.

In addition, there can be e.g. an intermediate storage compartment 48, a heating/ventilation/air-conditioning chamber 49, and a low-voltage switchgear chamber 50 housing a low-voltage switchgear 501, these chambers having chamber walls 480, 490, 500, 510. Additional compartments in the building 1 are exemplarily a mechanical workshop 6, a sewage room 7, fresh water pumps 8, a Diesel generator chamber 9, and living quarters 10.

Typically such station building 1 includes climate control installations to circulate, cool, dehumidify and filter air. Other equipment found in such a converter station building 1 include any of or a combination of fire extinguishing systems, barriers for fire and oil spills and general optical and acoustical alarms, control rooms and the like. Converter stations or generally buildings 1 of such or other types are used to convert electrical power lines from one voltage level to a different voltage level within the structure of public power distribution networks.

Air-insulated stations have to be designed with the electrical properties of air in mind. As a consequence such stations have a larger lay-out or footprint compared to gas-insulated stations to allow for larger distances between electrical active parts 401A, 401B; 401, 411, 421, 431; 441, 451, 461, 471 at different potentials. In gas-insulated stations all critical components are encapsulated in gas-tight housings filled with a suitable inert gas such as $SF_6$. Converter stations may be both, i.e. essentially air-insulated 401A with critical components being gas-insulated or encapsulated 401B.

The station of the example described below is essentially an air-insulated station. However the property of the air inside the station or inside single rooms or sections of the station are modified through the mixing of the air with a component, i.e. the dielectric insulation fluid, added to improve the insulation properties of the air. In the present example this dielectric insulation fluid is chosen for example from (but is not limited to) the family of perfluoroketones (PFK) known per se.

Figure 1:
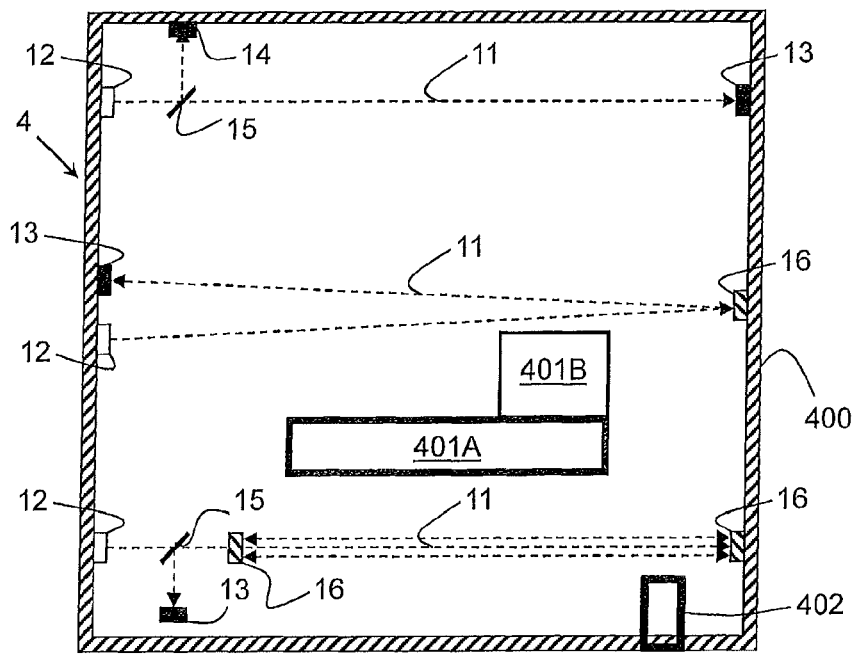
FIG. 1 illustrates examples of the invention using a collimated beam or beams of radiation across a room to be monitored.

As shown in FIG. 1, taking the example of a large equipment room 4 filled with a PFK gas mixture, the average concentration of PFK can be determined by for example directing a radiation beam 11 through the room 4 over a considerable path length of the room 4. The length of the path is selected so as to avoid measuring a local concentration of PFK and either over- or underestimating the true average concentration inside the room 4. The path length is approximately the distance between a source of radiation 12 and a detector 13. The source 12 and the detector 13 and their power supply lines and/or data and control lines (not shown) can be mounted on the wall 400 as shown, can be floor-mounted and/or can be suspended from the ceiling and/or be mounted onto parts of the permanently installed equipment.

In FIG. 1 three possible optical layouts or monitoring devices are shown exemplarily in a single room 4. In a normal installation it may suffice to chose only one of the set-ups or monitoring devices for the room monitoring. FIG. 1 can be regarded as a top view representing for example a horizontal cross-section at a short distance of 10 cm to 50 cm below the ceiling of room 4.

On the top (i.e. in a backward region of the room 4 when seen from the door or entrance 402) a single path installation is shown with the source 12 and detector 13 installed on opposite walls 101 of the room 4. A reference detector 14 can be used to provide independence of the measurement from the beam intensity $I_0$ by diverting a fraction of the beam onto the reference detector 14 using for example a beamsplitter 15.

The layout in the middle of FIG. 1 represents a double pass measurement with the source 12 and detector 13 being mounted on the same wall and a mirror 16 on the opposite wall. The path length is doubled compared to the above described example.

And the layout on the bottom of FIG. 1 represents a multi-pass setup or monitoring device wherein the beam 11 emanating from the source 12 is bounced between mirrors 16. The multipass setup can be realized in many different ways. For example, a cavity with two curved mirrors, such as in a White cell or a Herriot cell, but traversing along a substantial length of the room 4. The optics in a White cell or Herriot cell as such is disclosed in more detail in: "Tunable infrared laser spectroscopy", R. F. Curl and F. K. Tittel, Annual Reports Section C (Physical Chemistry) RSC Publishing, 98, pp. 219-272, 2002. The emitted light enters the cavity or cell through a partially transmitting mirror 16 (or through a hole in the mirror 16) and runs through the absorption path length multiple times, being reflected each time when it hits a mirror 16. Another partially transmitting mirror 16 then reflects part of the beam 11 that exits the cavity onto a detector 13. Alternatively, a cavity ring-down measurement can be run with a pulsed light source using, e.g., a confocal cavity.

It is also possible to use multiple beams to generate a light beam mesh throughout the room 4. The beams width can be expanded using suitable optics (wavelength dependent) in order to increase the absorption path volume. In this way, a larger sample of the dielectric insulation medium or gas inside the room 4 is interrogated. Beams can also be directed along locations where changes in PFK concentration are most likely, e.g. along open busbars or along the walls on which PFK condensation may occur at low outside temperatures.

From the light source 12 applicable for the chosen band of wavelength as described below a collimated beam 11 is generated and is directed through the room 4. The detector 13 is positioned at the end of the beam path and tracks the intensity continuously. Upon a change in PFK concentration, the transmitted intensity I will change and this change can be related to a decrease (or increase) in the PFK-molecule density within the beam path. To decouple the measurement from changes in light source intensity $I_0$ (e.g. due to aging), not the detected intensity I, but the normalized intensity or optical power $I/I_0$ can be logged. $I/I_0$ measurements are then translated into a PFK concentration using the known absorption length and the relevant PFK absorption cross-sections.

To save power, all of the measurement schemes disclosed herein can be operated in pulsed mode, too.

The source 12 and detector 13 can be tuned to operate at specific wavelengths or a wavelength band in the UV, in the near-IR or the mid-IR range, or more specifically in the spectral range of 200 nm to 400 nm, 1850 nm to 1950 nm, or 5000 nm to 20000 nm, or any combination(s) of these ranges.

Regarding the UV range of wavelengths it is known that C6 has a peak absorption at around 300 nm. It has further been found that the absorption peak for C5 in this range is shifted by about 5 nm, with the value for C7 being even closer to those of C6. The strong absorption cross-section and the specificity to ketones make this band a preferred candidate for optical monitoring a fluoroketone molecular concentration in a range of possible dielectric insulation gases. On the contrary the visible region does not seem particularly suitable for optical absorption measurements, as no specific absorption feature in the wavelength regime between 400 nm and 1100 nm were identified.

This band can be accessed using as light source 12 a gas discharge lamp, e.g. a deuterium lamp as commercially available (Ocean Optics DT-Mini-2-GS with appropriate filter), or UV LEDs that emit in a narrow spectral region as commercially available for example from Mightex, Toronto, Ontario Canada. Other UV light sources which can be used are excimer lamps (Xe) and NOx lamps (commercially available from Heraeus Noblelight or Analytical Control Instruments GmbH Berlin, Germany). The detector 13 for the UV band can be based on SiC photodiodes as commercially available for example from Roithner Lasertechnik GmbH, Vienna, Austria.

With regard to the near-infrared (NIR) spectral range it is found that C6 shows an absorption peak at 1891 nm, while C5 and C7 show two overlapping absorption peaks at 1873 nm/1882 nm and 1894 nm/1903 nm, respectively. There is no cross interference of the C5 absorption bands with those of $CO_2$ in the NIR region. $O_2$ does not have a permanent dipole moment and therefore does not exhibit a vibration spectrum in the infrared. The spectra of $CO_2$ (HITRAN data base) show a significant band at 1960 nm and at 2000 nm, which however do not overlap with the above fluoroketone bands. Water absorption lines can interfere with the C5 absorption line, but this depends on the specific optical setup of the analyzer (e.g. the spectral width of detection). Whether water interference causes a problem for the C5 detection of course depends on the relative absorption strength of the lines and the relative concentrations of C5 and water. However, according to this invention, water interference can be avoided completely by choosing appropriate sharp, narrow absorption features of for example C5 (or C6 or C7) that show no spectral overlap with the absorption features of water.

The NIR band can be accessed using as light source 12 incandescent or quartz halogen light bulbs, NIR LEDs or VCSELs (vertical cavity surface emitting laser), all of which are commercially available. The detector 13 for the NIR band can be based on Si or InGaS photodetectors as commercially available.

With regard to the mid-infrared (MIR) spectral range it is found that in the spectral region between 2000 cm−1 (5 μm) and 500 cm−1 (20 μm) C5 shows absorption bands between 600 cm−1 and 1900 cm−1. They presumably stem from vibrational transitions of the carbon framework (below about 1100 cm−1), of the C—F bonds (1100 cm−1 to 1400 cm−1) and the C=O carbonyl group (1800 cm−1). In the spectral region from 2000 cm−1 to 4000 cm−1, C5 does not display any absorption features. Some of these bands can be used for quantification of C5 by IR absorption.

It is advantageous to reduce cross-sensitivity to other species that may be present, such as water vapor, the carrier gas $CO_2$ and the expected decomposition products HF, $CF_4$, hexafluoropropene, heptafluoropropane. A particularly suitable band for the detection of C5 is that at around 990 cm−1 and/or at around 873.5 cm−1, and for C6 at around 1024 cm−1. Generally, a suitable wavelength or wavelength band for measuring the concentration of the dielectric insulation medium or fluid directly or in-situ can be established by comparing the respective spectra of the insulation fluid molecules, of the carrier gas molecules and of decomposition products thereof as caused by reactions at discharges etc.

For generating radiation in the mid-IR range the source 12 can include a broad-band, incandescent light source (e.g. a radiating filament) with a notch filter permitting the transmission of only selected wavelengths that interrogate a narrow spectral region in which the respective perfluoroketone absorbs. Other sources can include QCL (quantum cascade lasers) or lead salt diode lasers as known and commercially available. The detector 13 for the MIR band can be based on PbS photodetectors as commercially available.

To protect humans and equipment from the probing beam 11 directed across at least part of the room 4; 40-47, safety measures can be implemented including an automated shutdown of the source 12 in case of an opening of a door 402, having a parallel visible light beam alongside any invisible beams, locating the beams at a height not accessible by personnel during normal operations or having the beam 11 guided through solid guides which allow for an easy gas exchange, such as perforated tubes, but preventing human interference.

In embodiments, at least a part of the monitoring device 11-24, 211, in particular the electromagnetic of optical sensor 11, 21, 12, 22, 13, 23, 211, in particular a measurement channel or beam 11 and/or reference channel or beam 11 of the optical sensor 11, 21, 12, 22, 13, 23, 211, is separated from the room 4; 40-47 housing the electrical apparatus 401A, 401B; 401, 411, 421, 431; 441, 451, 461, 471 by an insulation-fluid-permeable protective cover, in particular an insulation-fluid-permeable and particle-impermeable protective cover (not explicitly shown). This protective cover is adapted to protect the optical sensor 11, 21, 12, 22, 13, 23, 211 from particle contamination present in the room 4; 40-47. It separates the monitoring device 11-24, 211, in particular an optical beam and/or optical components of the sensor 11, 21, 12, 22, 13, 23, 211, from the surrounding part of the room 4; 40-47. In addition, protective means such as gas adsorbers (e.g. comprising a zeolite) can be provided, if contaminants, e.g. decomposition gases, are created inside the room 4; 40-47 which may damage the optical sensor 11, 21, 12, 22, 13, 23, 211. In embodiments with such a protective cover, the protective cover comprises at least one of the group of a sintered material,
a porous material, for example a porous metal
a gauze,
a mesh,
a membrane, in particular comprising a polymer material, and
combinations thereof. Thus, an insulation-fluid-permeable and yet particle-impermeable protective cover is easier to realize.

In embodiments, the protective cover can be in the form of a protective cover plate (not explicitly shown), e.g. a plate separating the measurement channel or beam 11 and/or reference channel or beam 11 of the optical sensor 11, 21, 12, 22, 13, 23, 211, or can be in the form of a protective cover tube (not explicitly shown), e.g. a tube enclosing the optical sensor 11, 21, 12, 22, 13, 23, 211 or at least some of its optical elements 21, 12, 22, 13, 23, 211 and/or beam paths 11, in particular beam paths 11 of a measurement channel and/or reference channel. Any other form suitable to separate the optical sensor 11, 21, 12, 22, 13, 23, 211 from particles in the room 4; 40-47 is possible, as well.

In embodiments, the monitoring device 11-24, 211, in particular optical components thereof (e.g. beam 11, light source 12, 22, light detector 13, 23, 14, beam splitter(s) 15, mirror(s) 16), can be arranged (also e.g. via optical fiber) at a window (not shown) of the room 4; 40-47. Such a window can for example be a window in a wall 400; 400, 410, 420, 430; 440, 450, 460, 470 of the room 4; 40-47 or in a door 402, 412, 422, 432; 442, 452, 462, 472 of the room 4; 40-47. Thus, the window forms not only part of the room 4; 40-47, which houses the electrical equipment 401A, 401B; 401, 411, 421, 431; 441, 451, 461, 471, but also part of the monitoring device 11-24 or its optics. The window shall be transmissive at the measurement wavelength, and possibly also at the reference wavelength, e.g. by using glass with transmission in the near infrared or UV-transmitting material, such as quartz or sapphire, or mid infrared transmitting material, such as potassium bromide (KBr). In embodiments, a mirror or a reflective coating or another window for receiving transmitted light can be present in the room 4; 40-47.

To obtain a better estimate of the average PFK concentration, a distributed sensing system comprising multiple local concentration sensors can be adopted. For such a system, small optical sensors can be located at selected positions where for example changes in PFK concentration are expected to be large. It can be shown that an absorption path length of only 1 cm is already sufficient for a sensitive local measurement, and an average concentration of the molecule(s) to be monitored can be determined based on such local measurements that are distributed along a substantial length of the room 4.

Such a monitoring device with several local sensors arranged in the room sufficiently spaced apart allows for the use of relatively small optical PFK detectors of a volume of e.g. 10×10×10 cm³, housing light source, detector and local absorption path length. Such detectors can be positioned above and below doors, windows and near cold spots and hot spots (e.g. busbars or cooling pipes) to specifically monitor the PFK concentration in those areas.

Figure 2:
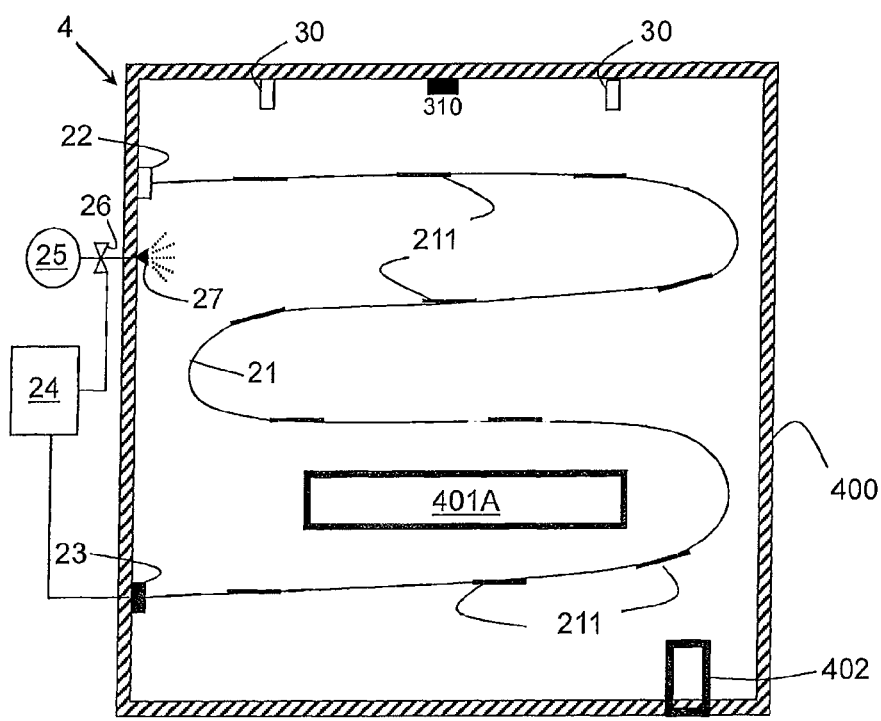
FIG. 2 illustrates an example of the invention using an optical fiber arranged across at least part of a room to be monitored.

As shown exemplarily in FIG. 2, an alternative to probing beams traversing throughout the entire room 4 or to a spatial distribution of local concentration sensors at multiple locations in a room 4 consist in using guided light beams, wherein the light is guided within a tube or bendable material, e.g. in an optical fiber 21, along a path within the room 4.

The schematic monitoring device shows a source 22 at one end of the optical fiber 21 and a detector 23 at its distal end. The optical fiber 21 includes at least one and preferably several sensing areas 211 at which the concentration of molecules, e.g. PFK molecules, can be measured. The sensing areas 211 can for example be exposed sections 211 of the optical fiber core where the cladding is removed. At these sections 211 the light beam travelling inside the optical fiber 21 can undergo attenuated total internal reflection (ATIR), the amount of which depends on the concentration of PFK outside the exposed optical fiber 21. This allows again a spatially distributed room monitoring for the molecular concentration of those molecules that provide higher dielectric strength than in air to the dielectric insulation medium present in the room 4.

Alternatively, special optical fibers 21 can be used, which are based on different physical effects, such as photonic crystal fibers 12, side hole fibers 12, Bragg grating fibers 12, etc., which are all known per se, but are herewith disclosed for the new purpose of concentration measurement of molecules.

However the interaction of gas and optical fiber 21 need not be limited to a plurality of discrete sensing areas 211, but can also occur in extended regions over the entire length of the optical fiber 21 or at least over a larger section of the optical fiber 21 to gain a spatially averaged molecule concentration measurement.

The optical sensors 11, 21, 12, 22, 13, 23, 211 used can be calibrated at the factory or in-situ. In order to calibrate the sensors of a system using an open beam 11 as described above, the sensor system is zeroed when the room 4 is free of PFK and a reference cell containing a known amount of PFK is placed in the beam 11. To compensate for aging of the light source 12, 22, a reflection from an optical surface (e.g. from the collimating or expanding lens) is used for normalization, generating the value $I_0$ introduced above.

In order to calibrate the detector 13, 23, a second light source situated close to the first light source can be used, emitting at a wavelength that does not overlap with the absorption band of the PFK or the carrier gas. The detector bandwidth is then chosen to cover also the reference light source. Because the reference light source does not age significantly as it is only turned on sporadically, it can be used as calibration standard for the detector performance. Alternatively, the reference light source can be positioned at the detector 13, 23 itself. The use of appropriate filters also allows the use of very broadband detectors: For PFK detection and for detector calibration, respectively, dedicated filters can be swung or rotated into the beam path in front of the detector 13, 23 automatically.

It is useful to embed the above systems for determining the concentration of PFK in a room 4 or building 1 within control systems 24 to respond automatically to a significant deviation of the to-be-monitored molecular concentration from a set value. However, before for example a global reduction in the concentration of PFK can be interpreted as being caused by dilution or leakage, a distributed temperature sensing 30 or a thermal imaging 30 of the room 4 can be performed. The temperature measurement is used to determine whether the temperature in parts of the room 4 is close to or below the condensation point of the original gas mixture in the room 4. The temperature control can be linked to a heating system, for example a closed-loop air conditioning system, which is activated to increase the room temperature above the condensation point.

A leakage as detected by the above systems for determining the concentration of PFK in a room 4 or building 1 can automatically initiate mitigating measures by the control unit 24 shown in FIG. 2. From the global or average PFK concentration measurement and the known volume of the room 4; 40-47 it can be estimated how much liquid PFK must be supplied to re-establish the nominal concentration. Liquid PFK can be supplied from a reservoir 25 and can be injected into the room 4 using for example an overhead nozzle array 27. The nozzles 27 are best heated, e.g. resistively by a heating wire wound around them, to assist rapid evaporation of a mist of PFK. The nozzles 27 or valves 26 in the supply line between the reservoir 25 and the nozzles 26 can be controlled by the control unit 24. Though shown in the context of FIG. 2, a control system 24 as described above can be added to any embodiment of the invention.

In embodiments, a or the control system 24 is connected to a temperature measuring system 30 for monitoring the temperature of the room 4; 40-47 at more than one location.

In embodiments, a or the control system 24 of the monitoring device 11-24, 211 is connected to at least one humidity sensor 310, e.g. a capacitive humidity sensor 310, arranged inside the room 4; 40-47 for measuring a humidity level in the room 4; 40-47. The measured humidity level is also transmitted to the control system 24. Thus, operating states can also be selected depending on the humidity level inside the room 4; 40-47.

The humidity sensor 310 or a method element of measuring the relative humidity can in particular be embodied using at least one of the group of:

A capacitive humidity sensor 310: Here, a variation of the dielectric constant of an appropriate hydrophilic material with water content is used as an indicator for the moisture level in the room 4; 40-47. The dielectric can be composed of metal oxides (e.g. $Al_2O_3$) or polymeric materials. As a prerequisite for material compatibility with, e.g., a fluoroketone in an insulation fluid component, polymeric sensing media must be immune for interaction with the insulation fluid components. This is also the case for dielectrics based on metal oxides.

A resistive humidity sensor 310: The variation of resistance or conductivity of humidity sensitive materials is addressed. With an increasing humidity, the resistance of the hygroscopic material decreases. Again, necessary precautions to avoid interference with the insulation fluid components must be taken, e.g. by functionalization of the used material.

An oscillating resonator humidity sensor 310 coated with a hygroscopic layer: In the presence of humidity, the mass loading on the oscillator changes, thus leading to a change in resonance frequency. The resonator coating must be chosen to only adsorb water, e.g. using silica gel or through direct surface functionalization (e.g. providing —OH groups that can engage in H-bonding with water).

A thermal conductivity humidity sensor 310: Absolute humidity can be quantified via a thermal conductivity of a reference insulation fluid (i.e. a dry insulation fluid) compared to the insulation fluid in the room 4; 40-47 which contains moisture. Considering that the insulation fluid is not supposed to change in composition during operation of the electrical apparatus 401A, 401B; 401, 411, 421, 431; 441, 451, 461, 471, humidity measurements are relatively easy to carry out as long as the only change in thermal conductivity will be induced by moisture. Otherwise, concentration changes can be accounted for by other measurements, in particular the optical measurement as disclosed herein.

A or the optical sensor 310; 11, 21, 12, 22, 13, 23, 211: As an example, infrared absorption measurements are well suited to track water vapor content without interfering with most insulation fluid components (see spectral data herein). As an example, there are infrared absorption bands of water available that do not overlap with those of the perfluoroketone C5 as insulation fluid component. These bands can be used for measuring the humidity in the room 4; 40-47.

In embodiments, in particular additionally, a system to create forced convection within the monitored room, such as a set of distributed fans, can be used to distribute the PFK evenly throughout the room 4.

Such a system to create forced convection within the monitored room 4 can also be used when a local reduction of PFK is detected, e.g. near a door 402 that has been opened, by one of the distributed concentration sensors 11, 21, 12, 22, 13, 23, 211 as described above. For that purpose it is advantageous that the monitoring system 11-24, 211 can for example be triggered directly and asynchronously with the intervals of a continuous measurement schedule by a door switch, trip or intrusion alarm systems etc.

In case of a local reduction in the concentration of PFK, a distributed fan system is activated to compensate the local loss of PFK at the expense of the global average PFK concentration in the room 4. For small regions subject to PFK depletion, the change in the global PFK concentration will not be considerable. If local PFK depletions exceeds a preset threshold, PFK injection can be initiated to compensate for the loss, either globally or through a local injection.

The control system 24 can also trigger acoustic or visible alarms or shut down electrical components 401A, 401B; 401, 411, 421, 431; 441, 451, 461, 471, trip switches etc. to prevent damage to the station 1 or its room 4; 40-47.

In more general terms, the monitoring device 11-24, 211 can be part of or can be connected to a control system 24 designed to detect a fault concentration outside an allowed concentration range of the molecules in the room 4; 40-47, in particular a fault concentration below a minimal threshold concentration of the molecules for a given operational state of the electrical apparatus 401A, 401B; 401, 411, 421, 431; 441, 451, 461, 471, and to automatically initiate mitigating measures in response to a deviation of the detected fault concentration from a minimal threshold concentration of the molecules.

In more general terms, the monitoring device 11-24, 211 with the sensor can have sensing means 11, 21, 12, 22, 13, 23, 211 that are arranged at two or more locations inside the room 4; 40-47 such that a transmission distance for electromagnetic radiation to be monitored is provided between the locations for sensing an averaged concentration of the molecules along the transmission distance between the locations, in particular wherein the transmission distance extends along a substantial length of the room 4; 40-47 or a length larger than a size of a door 402, 412, 422, 432; 442, 452, 462, 472 of the room 4; 40-47 or a length larger than a quarter length or even half length of the room 4; 40-47.

The sensor can also have sensing means 11, 21, 12, 22, 13, 23, 211 that are arranged in the room at opposing and/or adjacent walls 400; 400, 410, 420, 430; 440, 450, 460, 470 and/or at a ceiling and/or at a floor of the room 4; 40-47, in particular such that a collimated beam 11, 21 of electromagnetic radiation is transmitted across a free-space part or a full length of the room 4; 40-47.

The sensor can also have sensing means 11, 21, 12, 22, 13, 23, 211 comprising optical elements 12, 22; 13, 23; 15, 16, including a radiation source 12, 22 and a radiation detector 13, 23 and optionally a beamsplitter 15 and/or a mirror 16, that are arranged at different locations, for example at opposing or adjacent walls 400; 400, 410, 420, 430; 440, 450, 460, 470, in particular such that a collimated beam 11, 21 of electromagnetic radiation is transmitted across a free-space part or a full length of the room 4; 40-47.

The at least one sensor 11, 21, 12, 22, 13, 23, 211 can also include several sensors 11, 21, 12, 22, 13, 23, 211 being arranged along a substantial length of the room 4; 40-47 for monitoring an average of the concentration of the molecules PFK, in particular the several sensors 11, 21, 12, 22, 13, 23, 211 being arranged along a length larger than a size of a door 402, 412, 422, 432; 442, 452, 462, 472 for accessing the room 4; 40-47 by a human or along a length larger than a quarter length or even a half length of the room 4; 40-47.

Figure 3:
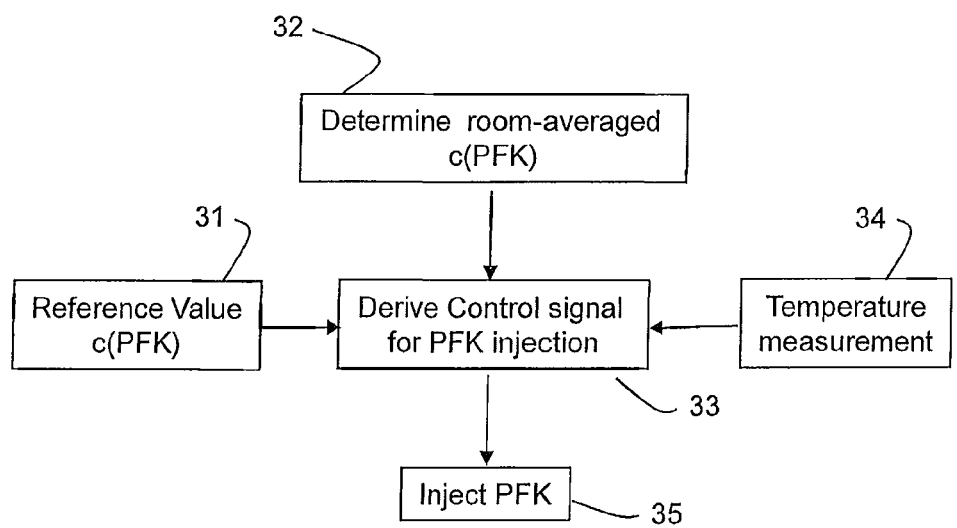
FIG. 3 is a flow chart with steps in accordance with an example of the invention.

FIG. 3 shows steps of the above method in an exemplary schematic flow chart. A normal or default value of a PFK concentration is set in step 31 depending on the tolerable dielectric breakthrough value for the electric field strength in the room 4; 40-47 or building 1. During operation a room-averaged or station-averaged concentration of PFK is continuously or essentially continuously measured (step 32). Depending on whether the temperature has dropped close or below the condensation point of the default air mixture (step 34) a control signal is derived (step 33) and serves for determining the amount of PFK to be injected (step 35) to reestablish the set concentration after the drop that occurred in the PFK concentration.

Throughout this application, the molecules to be monitored can be part of the dielectric insulation component C1 other than air that improve the dielectric strength of a background gas or carrier gas, e.g. of air, or can be part of decomposition products originating from any chemical transformation of the dielectric insulation medium under arcing or ageing or chemical reactions or the like in the room 4; 40-47.

Some more spectral details are disclosed in FIG. 5-15 that form a basis for the reliable measurement of concentration or density or number density or generally amount of the molecules present in the dielectric insulation medium or present in the room 4; 40-47 or in the building 1 to be monitored.

Figure 5:
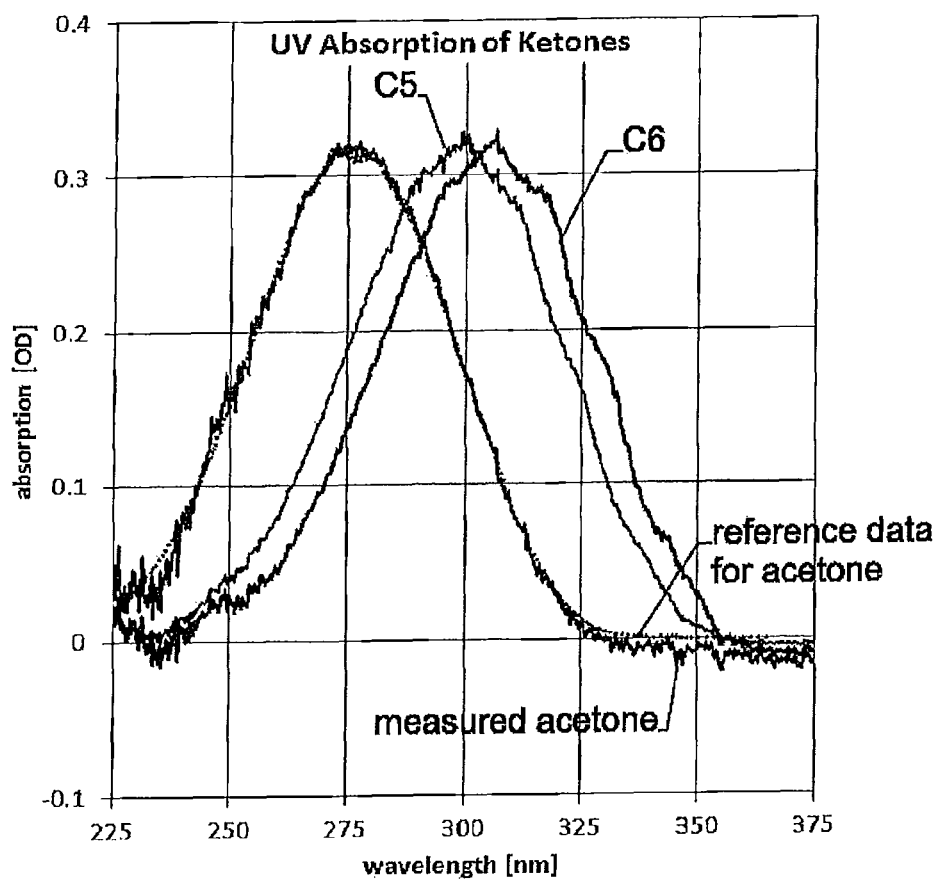
FIG. 5 shows an absorption diagram in the near UV range for "acetone", "C5", and "C6"

FIG. 5 shows an absorption diagram in the UV range for acetone, C5, and C6 together with reference data for acetone.

Figure 6:
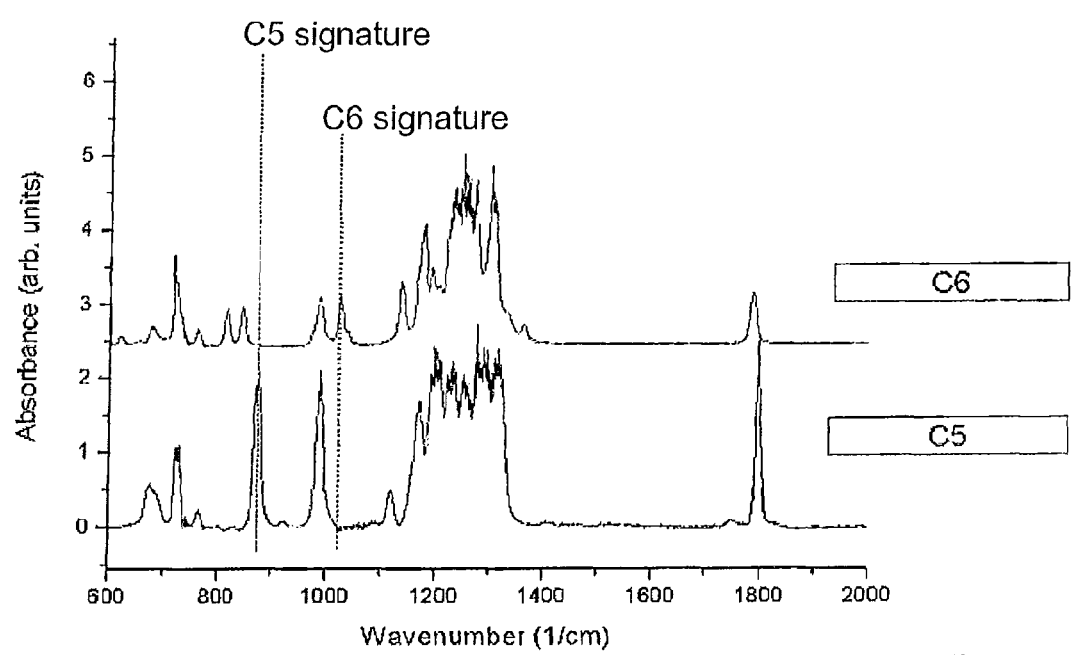
FIG. 6 shows an absorption diagram illustrating characteristic optical absorbance signatures of insulation fluid components "C5" and "C6" in the infrared region.

FIG. 6 shows an infrared absorption spectrum illustrating characteristic signatures of insulation fluid components C5 and C6 in the infrared region. The use of infrared spectroscopy offers an easy, specific, and accurate method for the determination (type and concentration) and monitoring of the fluid components that make up the insulation fluid. Many molecules, such as e.g C5 (i.e. C5-fluoroketone) and C6 (i.e. C6-fluoroketone) show characteristic spectral signatures (spectral fingerprint) in the infrared region which are, e.g., due to vibrational excitation. Specifically, measurements of the bands labeled C5-signature and C6-signature in the spectrum of the insulation fluid unambiguously indicate the presence and allow the concentration determination of C5 and/or C6, respectively. Note that the spectrum in the region 1200 $cm^{-1}$ to 1350 $cm^{-1}$ is partially saturated.

Figure 7:
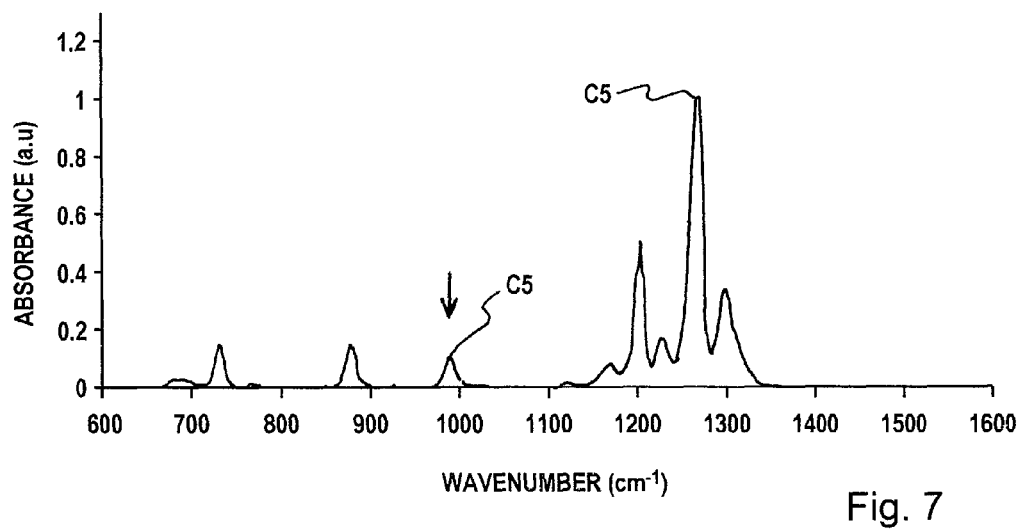
FIG. 7 shows an infrared absorption spectrum illustrating characteristic optical absorbance signatures of an insulation fluid component "C5"

FIG. 7 shows an infrared absorption spectrum illustrating characteristic optical absorption signatures of an insulation fluid component "C5". It is found that the insulation fluid component "C5" shows absorption peaks that do not overlap with spectral signatures of contaminants (indicated e.g. by the arrow, see below). Therefore, by selecting such an appropriate spectral signature, the insulation fluid component "C5" can be unambiguously monitored without cross-sensitivity to contaminants.

Figure 8:
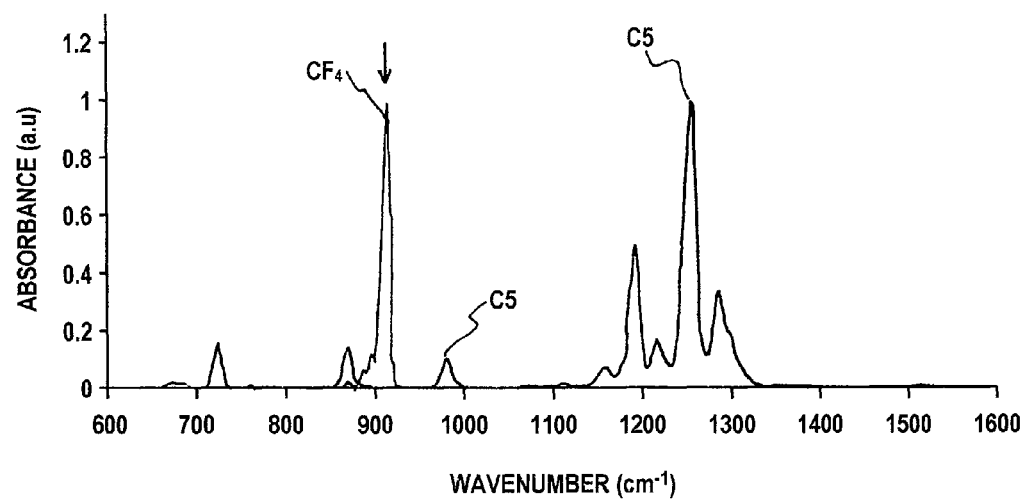
FIG. 8 shows infrared absorption spectra illustrating the characteristic optical absorbance signatures of the insulation fluid component "C5" of FIG. 7 as well as characteristic optical absorbance signatures of a contaminant "$CF_4$"

FIG. 8 shows infrared absorption spectra illustrating the characteristic optical absorbance signatures of the insulation fluid component "C5" of FIG. 7 as well as characteristic optical absorbance signatures of a contaminant "$CF_4$" (as indicated by the arrow). Because these peaks do not overlap, they allow an unambiguous detection of the contaminant "$CF_4$", even in the presence of "C5".

Figure 9:
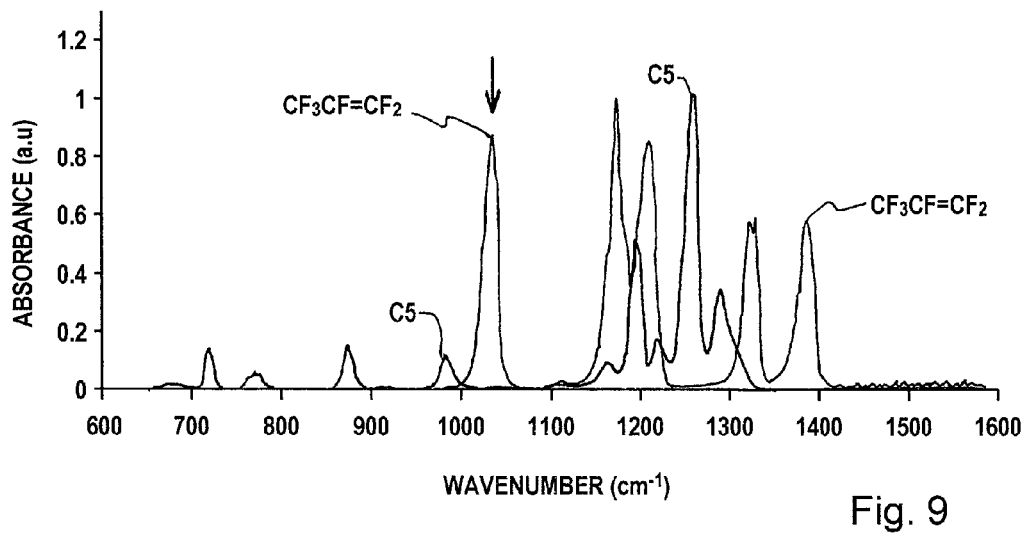
FIG. 9 shows infrared absorption spectra illustrating the characteristic optical absorbance signatures of the insulation fluid component "C5" of FIG. 7 as well as characteristic optical absorbance signatures of a contaminant hexafluoropropene "$CF_3CF=CF_2$"

FIG. 9 shows infrared absorption spectra illustrating the characteristic optical absorbance signatures of the insulation fluid component "C5" of FIG. 7 as well as characteristic optical absorbance signatures of a contaminant hexafluoropropene "$CF_3CF=CF_2$" (as indicated by the arrows). Similar to the situation in FIG. 8, these signatures allow an unambiguous detection of the contaminant "$CF_3CF=CF_2$", even in the presence of "C5".

Figure 10:
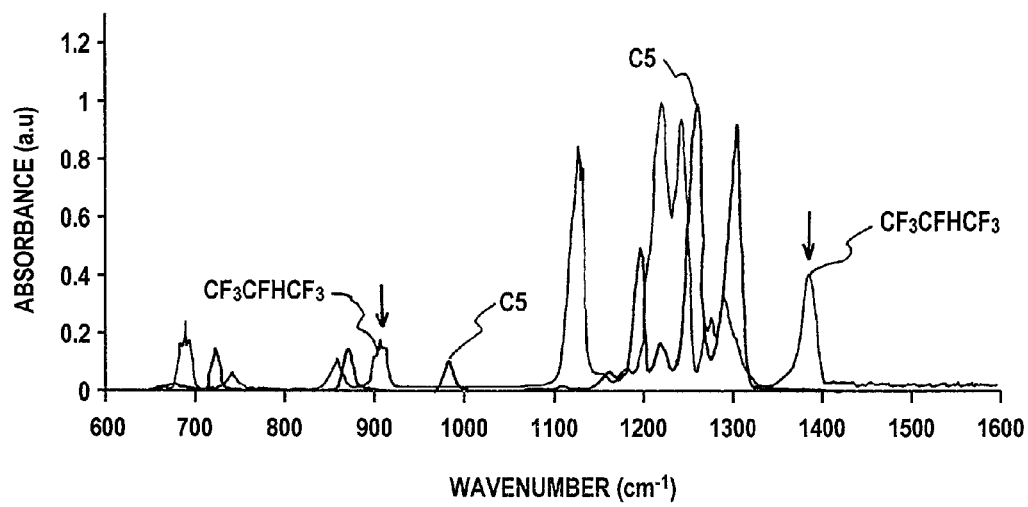
FIG. 10 shows infrared absorption spectra illustrating the characteristic optical absorbance signatures of the insulation fluid component "C5" of FIG. 11 as well as characteristic optical absorbance signatures of a contaminant heptafluoropropane "$CF_3CFHCF_3$"

FIG. 10 shows infrared absorption spectra illustrating the characteristic optical absorbance signatures of the insulation fluid component "C5" of FIG. 7 as well as characteristic optical absorbance signatures of a contaminant heptafluoropropane "$CF_3CFHCF_3$". Similar to the situation in FIGS. 8 and 9, these signatures allow an unambiguous detection of the contaminant heptafluoropropane "$CF_3CFHCF_3$", even in the presence of "C5".

Figure 11:
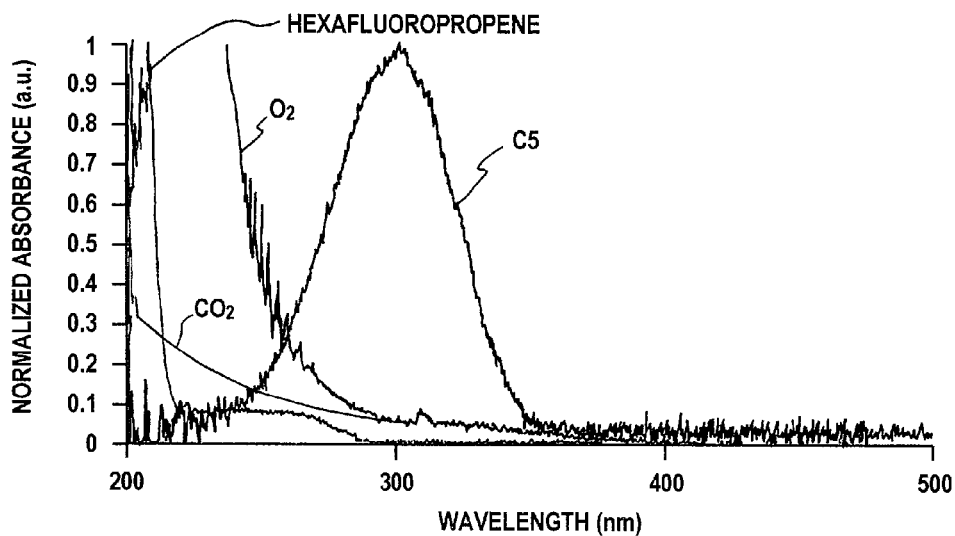
FIG. 11 shows absorption spectra of the insulation fluid components "C5", "$O_2$", and "$CO_2$", and of the contaminant "hexafluoropropene" for wavelengths between 200 nm and 500 nm.

FIG. 11 shows absorption spectra of the insulation fluid components "C5", "$O_2$", and "$CO_2$", and of the contaminant "hexafluoropropene" for wavelengths between 200 nm and 500 nm. The spectra of $O_2$ and $CO_2$ are from reference datasets while those of C5 and hexafluoropropene were measured. The spectral signatures of the contaminants "$CF_4$" and "heptafluoropropane" were also measured and did not show any spectral overlap with the UV absorption of "C5" (data not shown for clarity). As a conclusion, an optical absorbance measurement in the UV range is not hampered by these contaminants to a large degree, in particular if a narrow-band light source (e.g. an LED at around 300 nm with a full width at half maximum FWHM=12 nm) is used.

Figure 12:
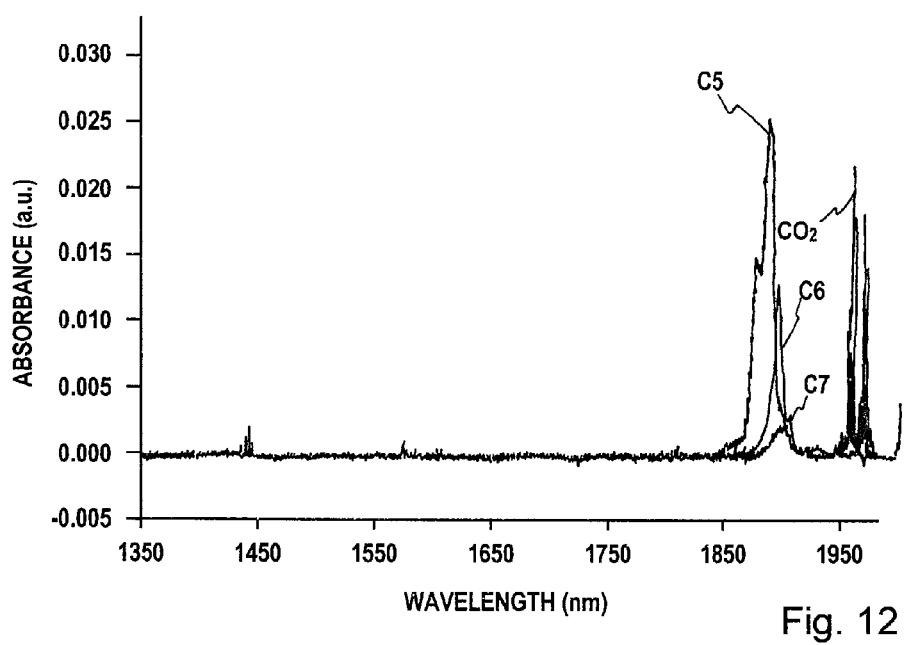
FIG. 12 shows absorbance spectra for insulation fluid components "C5", "C6", "C7", and "$CO_2$" for wavelengths between 1350 nm and 1950 nm.

FIG. 12 shows absorbance spectra for insulation fluid components "C5", "C6", "C7", and "$CO_2$" in the near infrared (NIR) region, specifically between 1350 nm and 1970 nm. A spectrometer from Axsun (Analyzer XLP910) was used for the spectral characterizations. The spectrometer is capable of recording the absorbance in the above-referenced wavelength region with a resolution of 3 $cm^{-1}$ which is equivalent to a wavelength resolution of about 1 nm.

Figure 13:
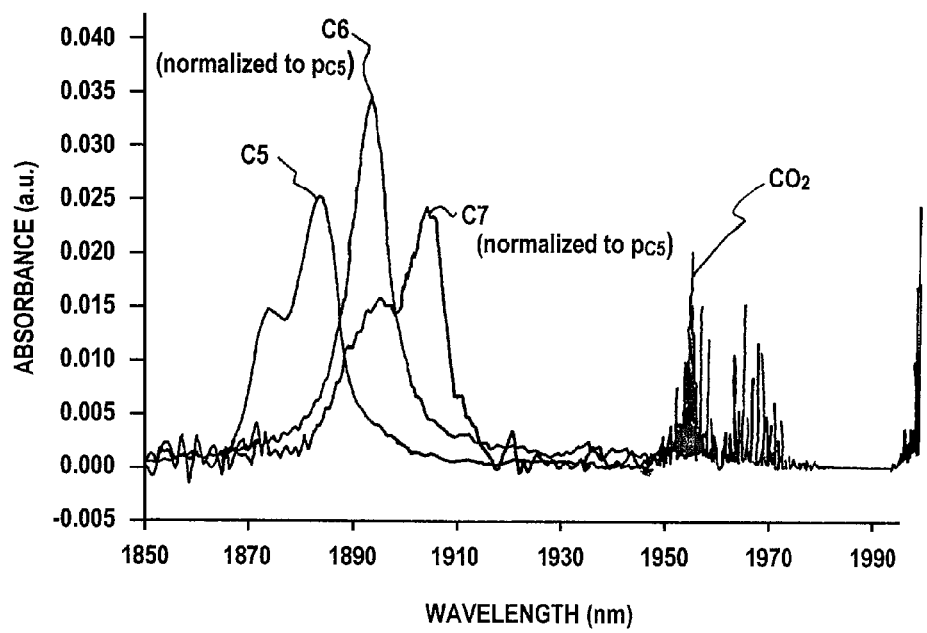
FIG. 13 shows a zoomed part of the spectra of FIG. 12 for wavelengths between 1850 nm and 1950 nm.

FIG. 13 shows a zoomed part of the spectra of FIG. 12 for wavelengths between 1850 nm and 1950 nm. As evident from FIGS. 12 and 13, the insulation fluid component "C6" shows an absorption peak at 1891 nm. The insulation fluid components "C5" and "C7" show two overlapping absorption peaks at 1873 nm/1882 nm and 1894 nm/1903 nm, respectively. These absorption bands are presumably second overtones of a C=O stretch vibration. $CO_2$ data on the right hand side of FIGS. 12 and 13 is reference data for comparison. Please note that the data in FIG. 13 is normalized to equal number density of molecules (i.e. $p_{C5}$=974 mbar).

Since the dielectric insulation medium or fluid can be a gas mixture of insulation fluid components including "C5", "$CO_2$", and "$O_2$" and since a specific analysis method for "C5" is advantageous, potential cross interference of the C5 absorption bands with those of $CO_2$ in the NIR region were checked for. $O_2$ does not have a permanent dipole moment and therefore does not exhibit a vibration spectrum in the NIR region. $CO_2$ shows a significant band at 1960 nm and around 2000 nm. These features, however, do not overlap with the C5 carbonyl band discussed above.

Thus, in summary, the identified absorption bands of C5 at 1873 nm/1882 nm represent a possible basis for a C5-specific NIR optical absorption measurement.

Figure 14:
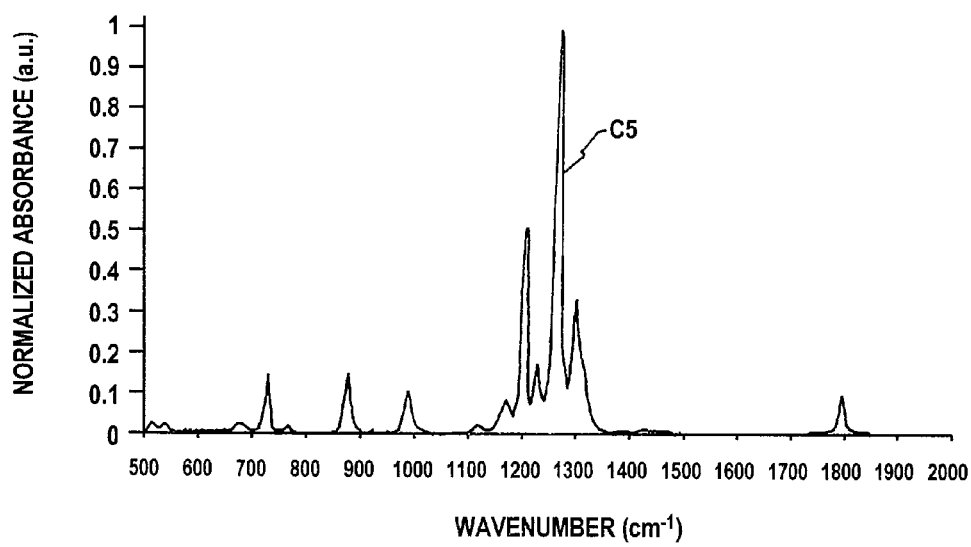
FIG. 14 shows an absorption spectrum of the insulation fluid component "C5" for wavenumbers between 500 $cm^{-1}$ and 2000 $cm^{-1}$.

FIG. 14 shows an absorption spectrum of the insulation fluid component "C5" for wavenumbers between 500 $cm^{-1}$ (wavelength 20 μm) and 2000 $cm^{-1}$ (wavelength 5 μm), i.e. in the mid infrared (MIR) region. For acquisition of the MIR spectra, a Fourier Transform Infrared Spectroscope (FTIR spectrometer, Digilab FTS-40 Pro, 0.5 $cm^{-1}$ resolution, 400-4000 $cm^{-1}$, 11.25 m path length, cell volume 0.005 $m^3$=5 liters) was used. To obtain good spectral separation of individual peaks and to avoid saturation, the pressures were reduced to several thousand Pa.

The infrared absorption of the insulation fluid component C5 in the spectral region between 4000 $cm^{-1}$ (2.5 μm) and 600 $cm^{-1}$ (16.6 μm) shows absorption bands between 600 $cm^{-1}$ and 1900 $cm^{-1}$. These absorption band presumably stem from vibrational transitions of the carbon framework (below about 1100 $cm^{-1}$), of the C—F bonds (1100 $cm^{-1}$ to 1400 $cm^{-1}$), and of the C=O carbonyl group (1800 $cm^{-1}$). In the spectral region from 2000 $cm^{-1}$ to 4000 $cm^{-1}$, C5 does not display any absorption features (data not shown).

Some of the above discussed bands can be used for quantification of the insulation fluid component C5 by IR absorption, for example by using a broad-band, incandescent light source and a notch filter permitting the transmission of only a selected wavelength that interrogates a narrow spectral region in which only C5 absorbs. For a measurement like this to work, cross-sensitivity to other insulation fluid components and contaminants that may be present should be excluded. As an example, insulation fluid components $O_2$ and $CO_2$ can be present. In addition, water vapor "$H_2O$" and the contaminants "HF", "$CF_4$", "hexafluoropropene", and "heptafluoropropane" may appear (note that there may be further contaminants that are not shown here). Further note that molecular oxygen does not have an infrared spectrum due to its lack of a permanent dipole moment (data not shown).

Figure 15:
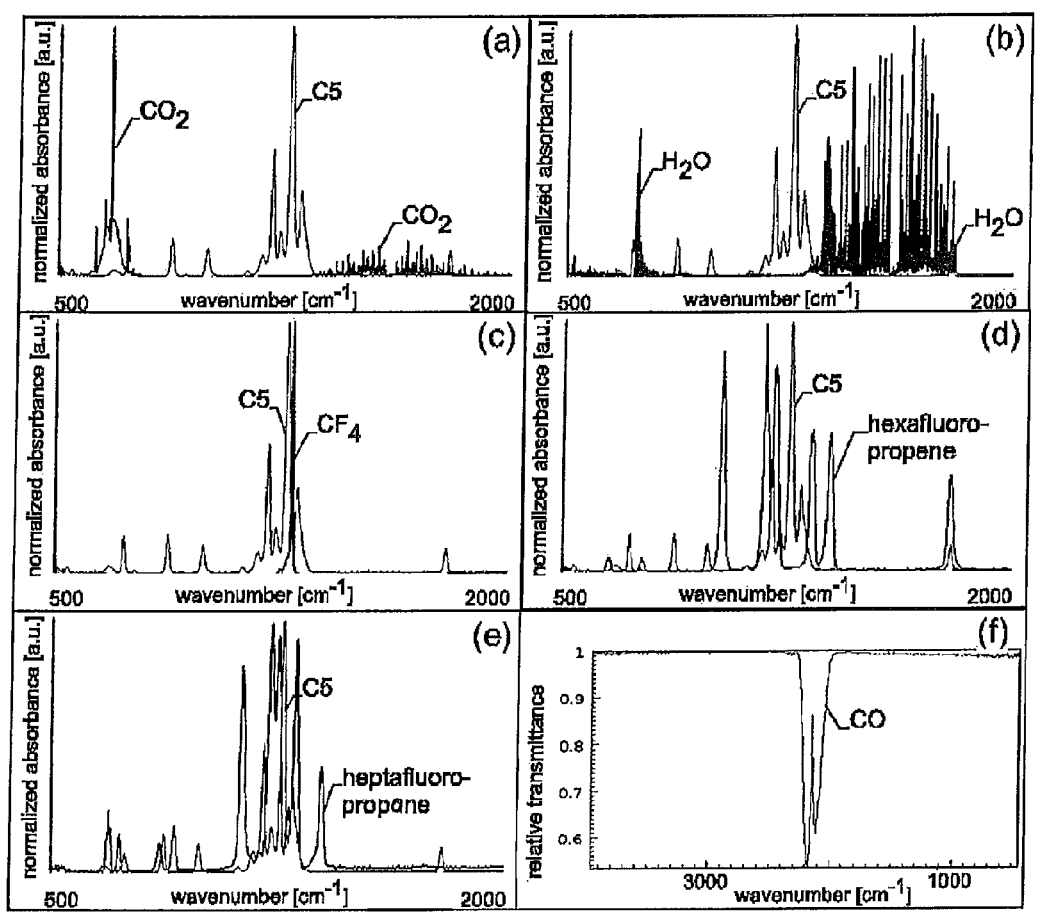
FIG. 15 shows the C5 spectrum of FIG. 14 overlapped with spectra of insulation fluid components "$CO_2$" and contaminants "$H_2O$", "$CF_4$", "hexafluoropropene", and "heptafluoropropane", and a relative transmittance of carbon monoxide "CO" as for wavenumbers between 2900 $cm^{-1}$ and 500 $cm^{-1}$.

FIG. 15 shows the C5 spectrum of FIG. 14 overlapped with spectra of insulation fluid components "$CO_2$" (FIG. 15a), of "$H_2O$" (FIG. 15b), and of contaminants "$CF_4$" (FIG. 15c), "hexafluoropropene" (FIG. 15d), and "heptafluoropropane" (FIG. 15e) as a function of wavenumbers between 2000 $cm^{-1}$ and 500 $cm^{-1}$. Furthermore, FIG. 15f shows a relative transmittance of "CO" as a function of wavenumbers between 2900 $cm^{-1}$ and 500 $cm^{-1}$ as a reference spectrum.

It is noted that infrared absorption measurements are well suited to track e.g. water vapor content without interference of the C5 content. This is because here are infrared absorption bands of water available that do not overlap with those of C5 and these can be addressed for monitoring (see FIG. 15b).

Not shown in FIG. 15 is the data of the contaminant "HF": The lowest vibrational transition of HF lies around 4000 cm$^{-1}$ and pure rotational transitions above 500 cm$^{-1}$ carry extremely small intensities at ambient temperatures.

The use of infrared spectroscopy for C5 detection is therefore herewith proven. However, great care shall be taken to avoid cross-sensitivities to other gas species by choice of appropriate spectral signatures. One suitable band for cross-interference-free C5 characterization is around 990 cm$^{-1}$. In addition, the absorption intensities and band shapes may vary slightly with temperature because of the temperature-dependence of the population of the rovibrational ground states given by the Boltzmann distribution. These effects should be taken into account.

In more general terms, the monitoring device 11-24, 211 can have a spectral sensitivity higher by a factor of at least 2, preferably by a factor of at least 10, for the molecules to be monitored than for the dielectric insulation medium other than the molecules to be monitored.

Figure 16:
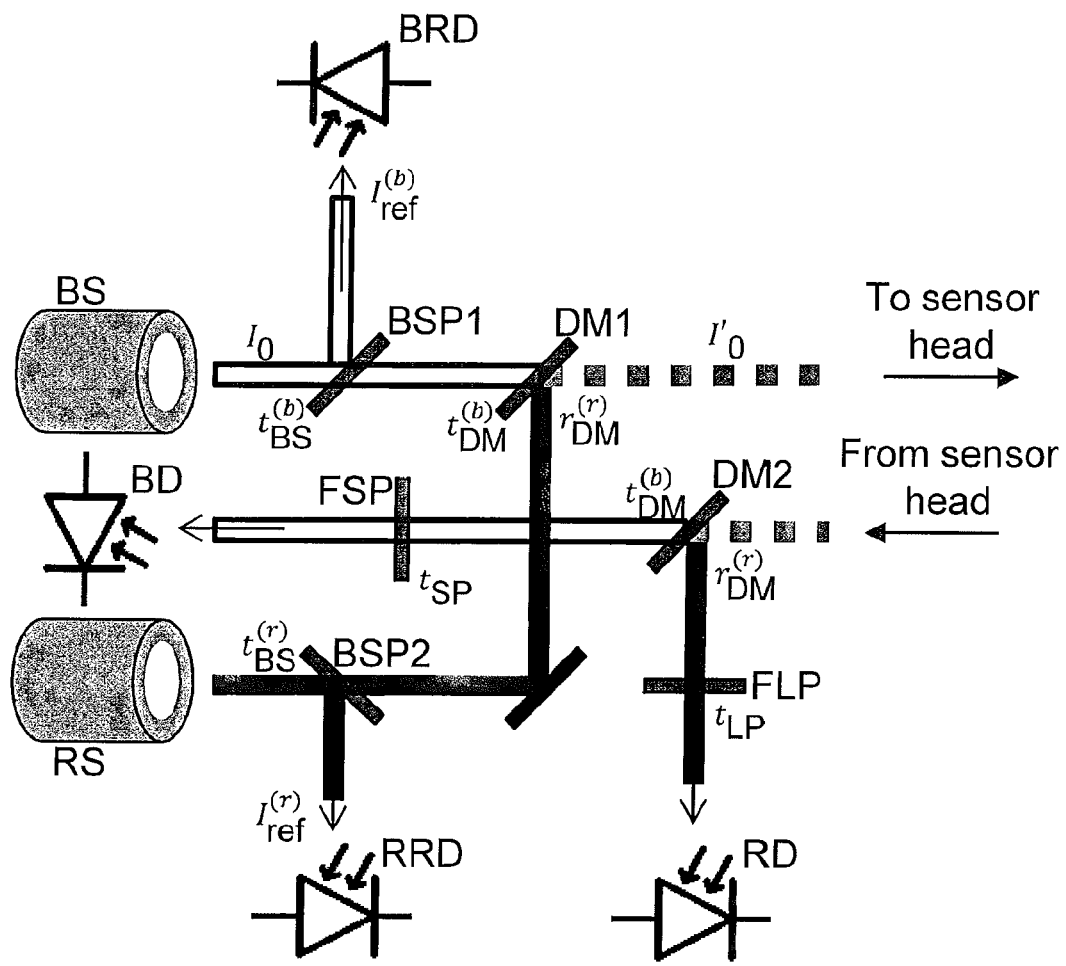
FIG. 16 shows an optical sensor with an optical measurement channel and an optical reference channel.

FIG. 16 shows an embodiment of an optical sensor (for example an optical sensor 11, 21, 12, 22, 13, 23, 211 of FIG. 1 or FIG. 2) with an optical measurement channel or beam at a first wavelength (e.g. that is modified, in particular absorbed, by the first fluid component (A)), and an optical reference channel or beam at a second wavelength that is not modified, in particular not absorbed, by the first fluid component (A), in particular fluoroketone. Several factors could adversely affect the measurements:

light source emission drift (wavelength and intensity e.g. due to aging, internal temperature and surrounding temperature)
  optical fiber transmission changes (e.g. due to bending losses, physical movement of fibers, stress, temperature)
  transmission changes at optical connectors (e.g. due to physical movement, mechanical shock, vibration, stress, temperature)
  transmission changes at optical interfaces (e.g. due to contamination)
  optical detector instability (e.g. due to aging)
  analyzer electronics instabilities (e.g. affected by electromagnetic interference or e.g. due to ageing)

are easier to correct for. Thus, the precision and reliability of the optical measurement can be improved.

The first five factors can be mitigated by using an optical reference channel integrated into the optical sensor 11, 21, 12, 22, 13, 23, 211.

A blue light source BS emitting at around 293 nm (open rectangles), i.e. within the absorption band of e.g. C5 as first insulation fluid component A, is coupled to an optical fiber (not shown) which delivers the light to an optical probe (sensor head). Alternatively, the blue light source BS is directly mounted to an optical feedthrough directing the light through the measurement path or beam 11 in fluid communication with the room 4; 40-47 (see above).

Prior to being coupled into the optical fiber or the measurement channel or beam 11, part of the light from the blue light source BS is split off using an optical beam splitter BSP1 and is send to a blue reference detector BRD which measures the stability of the emitted light intensity of the blue light source BS.

To eliminate artifacts in the transmitted signal (such as changes in the fiber bending losses or the presence of particle contamination on the optical interfaces within the room 4; 40-47), a reference channel is used.

Light at a slightly red-shifted wavelength (black beams) which is not absorbed by e.g. C5 as first insulation fluid component A, i.e. at wavelengths λ>360 nm, emitted by a red light source RS is used to interrogate the optical path for optical transmission changes. The emission stability of RS is recorded by a red reference detector RRD using a second beam splitter BSP2.

The red and blue light is combined (e.g. by a first dichroic mirror DM1). The red light traverses the same optical path (hatched beams) as the blue light, but is not absorbed by the insulation fluid component A (e.g. C5). When the red light returns from the sensor head, it is split off using a second dichroic mirror DM2 to the red light detector RD. To ensure that none of the red light falls onto the blue light detector BD and vice versa, a short pass filter FSP is arranged in front of the blue light detector BD and a long pass filter FLP is arranged in front of the red light detector RD.

The number density of the insulation fluid component A (e.g. C5) can be obtained from the transmitted intensities, and at the same time losses introduced in the optical paths and variations in the intensity of the light sources can be corrected for. In particular the following formula can be used:

$$I_{tr}^{(b)} = t_{SP} t_{DM}^{(b)} \left\{ \left[ \frac{t_{DM}^{(b)} t_{BS}^{(b)} I_{ref}^{(b)}}{1 - t_{BS}^{(b)}} + \frac{k}{2} \left( \frac{I_{tr}^{(r)}}{t_{LP} r_{DM}^{(r)}} - \frac{r_{DM}^{(r)} t_{BS}^{(r)} I_{ref}^{(r)}}{1 - t_{BS}^{(r)}} \right) \right] e^{-\sigma l N} + \frac{k}{2} \left( \frac{I_{tr}^{(r)}}{t_{LP} r_{DM}^{(r)}} - \frac{r_{DM}^{(r)} t_{BS}^{(r)} I_{ref}^{(r)}}{1 - t_{BS}^{(r)}} \right) \right\}$$

with $I_{tr}(b)$=transmitted blue light intensity (falling onto blue light detector BD)

$t_{SP}$=transmissivity of short pass filter FSP $t_{DM}(b)$=transmissivity of dichroic mirror DM1, DM2 for blue light $t_{BS}(b)$=transmissivity of beam splitter BSP1 for reference blue light (to blue reference detector BRD)

$I_{ref}(b)$=reference blue light intensity (falling onto blue reference detector BRD)

k=conversion factor for wavelength dependence of optical losses, defined by $k=\Delta I_{loss}(b)/\Delta I_{loss}(r)$ with $\Delta I_{loss}(b)$=blue light intensity losses on forward optical path to the gas (i.e. reduction of blue light intensity after BSP1 and DM1 by losses up to gas) and on the backward optical path from the gas to the detector BD (i.e. reduction of sensor return blue light intensity by losses) and $\Delta I_{loss}(r)$=red light intensity losses on forward optical path to the gas (i.e. reduction of red light intensity after BSP1 and DM1 by losses up to gas) and on backward optical path from the gas to the detector RD (i.e. reduction of sensor return red light intensity by losses)

$I_{tr}(r)$=transmitted red light intensity (falling onto red light detector RD)

$t_{LP}$=transmissivity of long pass filter FLP $r_{DM}(r)$=reflectivity of dichroic mirror DM1, DM2 for red light $t_{BS}(r)$=transmissivity of beam splitter BSP2 for reference red light (to red reference detector RRD)

$I_{ref}(r)$=reference red light intensity (falling onto red reference detector RRD)

σ=absorption cross section of dielectric insulation fluid component A (e.g. C5)

l=absorption path length (in gas; in absorbing gas at at least one wavelength)

N=number density of dielectric insulation fluid component A (e.g. C5).

A periodic measurement, e.g. a pulsed measurement, is preferable to minimize temperature-induced drift effects on the light sources. In this context, it is practical to alternate between the red and the blue channel. Then, by time-gated detection (e.g. via a lock-in amplifier), the red light detector RD, one dichroic mirror and the filters FLP and FSP can be omitted using just one common detector for both beams, given that detector sensitivity at the different wavelengths is sufficient or similar and the ratio of those sensitivities is known.

Electronics, i.e. light source and detector, can be arranged at the optical components. In this case, proper shielding from electromagnetic radiation is necessary. If electronics cannot be shielded from electromagnetic radiation from the electrical apparatus 1, a fiber optic link can be used. In that case the reference channel setup is particularly useful, if the fibers cannot be held rigidly in place. Alternatively or in addition, they can be immobilized in a duct. In any case, whether the system requires fiber optic links depends on whether electromagnetic interference is critical or not or can be shielded or not.

Definitions:

In particular, the term "air" herein includes "technical air", i.e. pressurized and dried ambient air, or "synthetic air", i.e. mixtures of nitrogen ($N_2$) and oxygen ($O_2$) with various mixing ratios, or ambient air.

While there are shown and described presently preferred embodiments of the invention, it is to be understood that the invention is not limited thereto but may be otherwise variously embodied and practised within the scope of the following claims. In particular, disclosed device features herewith also disclose the corresponding method features, and disclosed method features herewith also disclose the corresponding device features.

LIST OF REFERENCE SYMBOLS 1 converter station, converter building
1a helicopter platform
2 building wall (e.g. with staircase)
3 basement construction
4; 40-47 room
40 valve hall
41 reactor hall
42 DC hall
43 valve hall
44 GIS hall
45 cable hall
46 transformer hall
47 arrestor hall
48 intermediate gas storage compartment
49 heating/ventilation/air-conditioning chamber
50 low-voltage switchgear chamber
51 electrical supply chamber
400; 400, 410, 420, 430; 440, 450, 460, 470 wall of halls, room wall
480, 490, 500, 510 chamber wall, compartment wall
401A, 401B; 401, 411, 421, 431; 441, 451, 461, 471 electrically active part, medium- or high-voltage apparatus
401A electrical apparatus, high-voltage apparatus or device, medium-voltage apparatus or device
401B non-encapsulated component of the electrical apparatus
401 power semiconductor valve(s)
411 reactor
421 DC electrical active part
431 power semiconductor valve(s)
441 GIS switchgear
451 cables
461 transformers
471 arrestors
501 low-voltage switchgear
402, 412, 422, 432; 442, 452, 462, 472 opening; opening for human being, door
403, 413, 423, 433; 443, 453, 463, 473 sealing means, door sealing
6 mechanical workshop
7 sewage room, sludge tank
8 fresh water pumps
9 Diesel generator chamber
10 living quarter
11-24, 211 monitoring device
11 beam, optical beam
12, 22 radiation source
13, 23 radiation detector
14 reference detector
15 beam splitter
16 mirror
21 optical fiber
211 active fiber section(s)
24 control unit
25 reservoir
26 valve
27 nozzle, spraying nozzle
30 temperature measuring system, non-local temperature measuring system
310 humidity sensor
Step 31 Set reference value
Step 33 Generate control signal
Step 34 Determine room temperature
Step 35 Inject PFK

The invention claimed is:

1. A system for monitoring a concentration of molecules present in a dielectric insulation medium in a room housing at least one medium voltage or high voltage electrical apparatus and being accessible by humans, comprising:
a monitoring device including at least one radiation sensor and a radiation source;
the monitoring device determining, via the at least one radiation sensor, in a non-local manner an averaged concentration-dependent electromagnetic property of the molecules present in the dielectric insulation medium at at least one wavelength or wavelength band of the electromagnetic wave spectrum, the dielectric insulation medium being an organic fluorine compound;
wherein the monitoring device determines the concentration of the molecules of the organic fluorine compound and monitors, in-situ, a dielectric strength of the dielectric insulation medium inside the room;
a controller, that is part of or connected to the monitoring device, controlling the dielectric strength of the dielectric insulation medium inside the room, the controller designed to detect, from the monitoring device, a fault concentration outside an allowed concentration range of the molecules in the room and to automatically initiate mitigating measures in response to changes in the concentrations of the dielectric insulation medium, the mitigating measures including injection of the dielectric insulation medium into the room, and
a supply system, including a reservoir and a nozzle, connected to the controller for a controlled injection of the dielectric insulation medium into the room.

2. The system of claim 1, wherein the monitoring device is adapted to determine as the concentration-dependent electromagnetic property an emission and/or an absorption and/or a transmission and/or a scattering by the molecules.

3. The system of claim 1, wherein the monitoring device determines
the concentration of the molecules, that are part of a dielectric insulation component C1 other than air or that provide to the dielectric insulation medium a dielectric strength greater than the dielectric strength of air, or
the concentration of such molecules, that are not part of a background gas present in the dielectric insulation medium, and that are not any one of the group consisting of: nitrogen, oxygen carbon dioxide, or
the concentration of such molecules that originate from chemical transformation of the dielectric insulation medium under arcing or ageing or chemical reactions in the room, or
the concentration of a partly fluorinated or fully fluorinated compound of an olefine, an alkane, a ketone or polyketone, an ether or polyether, and any mixtures thereof, or
the concentration of a partly fluorinated or fully fluorinated fluoroketone comprising exactly 5 or exactly 6 or exactly 7 or exactly 8 carbon atoms and any mixtures thereof.

4. The system of claim 1, the monitoring device having a spectral sensitivity higher by a factor of at least 2 for the molecules to be monitored, the molecules to be monitored being molecules of a perfluoroketone, than for molecules of a background gas present in the dielectric insulation medium.

5. The system of claim 4, the monitoring device having the spectral sensitivity higher by a factor of at least 10 for the molecules to be monitored, the molecules to be monitored being molecules of the perfluoroketone, than for the molecules of the background gas present in the dielectric insulation medium.

6. The system of claim 1,
wherein the at least one wavelength or wavelength band is in a spectral range of 200 nm to 20000 nm, or
wherein the at least one wavelength or wavelength band is in at least one of the spectral ranges: 200 nm to 400 nm, 1850 nm to 1950 nm, and 5000 nm to 20000 nm.

7. The system of claim 1,
wherein the sensor has sensing means for measuring an averaged emission and/or an averaged absorption and/or an averaged transmission by the molecules along a length in the room, the length being larger than a size of a door for accessing the room by a human or larger than a quarter length or even a half length of the room, and/or
wherein the sensor has sensing means that are arranged at two or more locations inside the room such that a transmission distance for electromagnetic radiation to be monitored is provided between the locations for sensing an averaged concentration of the molecules along the transmission distance between the locations, wherein the transmission distance extends along a length in the room, the length being larger than a size of a door of the room or larger than a quarter length or even half length of the room.

8. The system of claim 1, wherein the sensor has sensing means that are arranged in the room at opposing or adjacent walls or at a ceiling or a floor of the room, such that a collimated beam of electromagnetic radiation is transmitted across a free-space part or a full length of the room, or
wherein the monitoring device comprises optical elements, including the radiation source, the at least one radiation sensor, a beamsplitter, and a mirror, that are arranged at different locations such that a collimated beam of electromagnetic radiation is transmitted across a free-space part or a full length of the room.

9. The system of claim 1, wherein the sensor has sensing means, that are permanently installed in the room and/or that are arranged in an eye-safe region of the room and/or that are arranged in a region of the room that is not accessible by up-right walking humans.

10. The system of claim 1, wherein the sensor has sensing means, that are arranged in regions of above-average field strengths in the room and/or that are arranged along non-encapsulated components of the electrical apparatus.

11. The system of claim 1,
wherein the at least one radiation sensor includes several sensors being arranged along a length in the room for monitoring an average of the concentration of the molecules, the length being larger than a size of a door for accessing the room by a human or larger than a quarter length or even a half length of the room, or
wherein the at least one radiation sensor includes an optical fiber arranged within the room to be monitored, wherein the optical fiber includes at least one active section at which a beam in the optical fiber interacts with the surrounding dielectric insulation medium, the dielectric insulation medium being a gas.

12. The system of claim 1, the controller designed to detect a fault concentration below a minimal threshold concentration of the molecules for a given operational state of the electrical apparatus, and to automatically initiate mitigating measures in response to a deviation of the detected fault concentration from the minimal threshold concentration of the molecules.

13. The system of claim 1,
wherein a or the controller is connected to a temperature sensor monitoring the temperature of the room at more than one location, and/or
wherein the controller is connected to a supply system for a controlled injection of the molecules into the room.

14. The system of claim 1,
wherein the monitoring device is adapted to the room to monitor an average, being a spatially continuous average and/or a sampling-point average, of the concentration of the molecules, which are present in the dielectric insulation medium in the room, along an averaging path length in the room,
wherein the averaging path length is of the order of a dimension of the room, or of a dimension of a door for accessing the room by a human, or of a dimension of the at least one medium-voltage or high-voltage electrical apparatus.

15. The system of claim 1, the monitoring device being adapted to determine the concentration of at least one component selected from the group consisting of:
partially or fully fluorinated ethers, including: hydrofluoroethers, hydrofluoro monoethers, hydrofluoro monoethers containing at least 3 carbon atoms, perfluoro monoethers, perfluoro monoethers containing at least 4 carbon atoms, fluorooxiranes, perfluorooxiranes, hydrofluorooxiranes, perfluorooxiranes comprising from three to fifteen carbon atoms, hydrofluorooxiranes comprising from three to fifteen carbon atoms, and mixtures thereof;

partially or fully fluorinated ketones, including: hydrofluoro monoketones, perfluoro monoketones, perfluoro monoketones comprising at least 5 carbon atoms, and mixtures thereof;

fluoroolefins, including: perfluoroolefines, hydrofluoroolefins (HFO), hydrofluoroolefins (HFO) comprising at least three carbon atoms, hydrofluoroolefins (HFO) comprising exactly three carbon atoms, trans-1,3,3,3-tetrafluoro- 1-propene, 2,3,3,3-tetrafluoro- 1-propene, and mixtures thereof; and mixtures thereof.

16. The system of claim 1, wherein the monitoring device includes a light source and the sensor comprises an optical measurement beam at a first wavelength, and an optical reference beam at a second wavelength that is not absorbed by a first fluid component being fluoroketone.

17. The system of claim 1, wherein a or the controller of the monitoring device is connected to at least one humidity sensor in the room; the humidity sensor being selected from the group consisting of:
    a capacitive humidity sensor,
    a resistive humidity sensor,
    an oscillating resonator coated with a hygroscopic layer,
    a thermal conductivity sensor,
    a or the optical sensor,
    and combinations thereof.

18. A building, in particular converter building, comprising:
    at least one room having a solid room wall enclosing an interior space and at least one electrical active part contained in the interior space, the room wall having at least one opening, which is designed such that the opening allows a human to enter the interior space, wherein the interior space contains a dielectric insulation medium comprising a dielectric insulation component C1 other than air,
    the room being equipped with a monitoring device for monitoring a concentration of molecules present in the dielectric insulation medium, and the monitoring device comprises a radiation source and at least one radiation sensor for determining a concentration-dependent electromagnetic property of the molecules present in the dielectric insulation medium at at least one wavelength or wavelength band of the electromagnetic wave spectrum,
    the opening is sealable, the room wall encloses the interior space in a gas-tight manner when the opening is sealed, and
    the monitoring device in-situ monitoring a dielectric strength of the dielectric insulation medium inside the room and controlling, via a controller, the dielectric strength of the dielectric insulation medium inside the room.

19. The building of claim 18, wherein the sensor of the monitoring device has sensing means for measuring a concentration-dependent optical emission and/or optical absorption and/or optical transmission by the molecules to be monitored.

20. The building of any one of the claims 18 to 19, wherein the molecules are part of the dielectric insulation component C1 other than air; and/or the molecules are not part of a background gas present in the dielectric insulation medium and wherein the molecules are not any of the group consisting of: nitrogen, oxygen carbon dioxide, or
    wherein the molecules to be monitored provide a dielectric strength to the dielectric insulation medium larger than the dielectric strength of air; and/or the monitoring device is for in-situ monitoring and/or controlling an average dielectric strength of the dielectric insulation medium inside the room.

21. The building of any of the claims 18 to 19, wherein the monitoring device is arranged inside the room in regions of above-average dielectric field strengths and/or is arranged along non-encapsulated components of the electrical apparatus.

22. The building of any of the claims 18 to 19, wherein
    the room is accessible by humans without deteriorating a dielectric strength of the dielectric insulation medium in the room below an operational threshold value of the electrical active parts; and/or
    the room is accessible by humans while maintaining a dielectric strength of the dielectric insulation medium in the room above a dielectric strength of air; and/or
    the dielectric insulation medium inside the room is non-toxic and breathable, particularly at a pressure close to ambient atmospheric pressure.

23. The building of any of the claims 18 to 19, wherein the monitoring device is permanently installed inside the room.

24. A method of monitoring the concentration of molecules present in a dielectric insulation medium in a room, the method being executed by a monitoring system of claim 1, the room being accessible by humans, the method comprising the steps of:
    monitoring in-situ the concentration of the molecules in the dielectric insulation medium, the dielectric insulation medium being a dielectric insulation fluid or gas comprised of an organic fluorine compound, by determining in a non-local manner, via the at least one radiation sensor of the monitoring device, an averaged concentration-dependent electromagnetic property of the molecules in the dielectric insulation medium at at least one wavelength of the electromagnetic wave spectrum, wherein
    the room houses at least one medium-voltage or high-voltage electrical apparatus, and wherein
    the monitoring is for in-situ monitoring a dielectric strength of the dielectric insulation medium inside the room;
    detecting, with the controller, a fault concentration outside an allowed concentration range of the molecules in the room and to automatically initiate mitigating measures in response to changes in the concentrations of the dielectric insulation medium, and the controller being connected to the supply system for the controlled injection of the dielectric insulation medium into the room; and
    delivering the dielectric insulation medium to the room by controlling the supply of the dielectric insulation medium.

25. The method of claim 24, wherein determining the concentration-dependent electromagnetic property comprises determining an emission and/or an absorption and/or a transmission and/or a scattering by the molecules.

26. The method of any of the claims 24 to 25, wherein the determining comprises measuring an emission and/or an absorption and/or a transmission by the molecules along a length in the room, the length being larger than a size of a door for accessing the room by a human or larger than a quarter length or even a half length of the room.

27. The method of any one of the claims 24 to 25, wherein further the monitoring device is for in-situ monitoring and/or controlling an average dielectric strength of the dielectric insulation medium inside the room.

28. The method of any one of the claims 24 to 25, further comprising the step of monitoring a temperature of the room at more than one location to determine whether the temperature at a location is close or below the condensation temperature of a standard atmosphere comprising a desired concentration of the dielectric insulation fluid.

29. The method of any one of the claims 24 to 25, wherein the molecules in the dielectric insulation medium are a perfluoroketone, more particularly a partly fluorinated or fully fluorinated fluoroketone comprising exactly 5 or exactly 6 or exactly 7 or exactly 8 carbon atoms and any mixtures thereof.

* * * * *